United States Patent [19]

McGinity et al.

[11] Patent Number: 5,227,157
[45] Date of Patent: Jul. 13, 1993

[54] DELIVERY OF THERAPEUTIC AGENTS

[75] Inventors: James W. McGinity, Austin, Tex.; Susan L. Ashley, Overland Park, Kans.

[73] Assignee: Board of Regents, The University of Texas System, Austin, Tex.

[21] Appl. No.: 388,321

[22] Filed: Jul. 31, 1989

Related U.S. Application Data

[63] Continuation-in-part of Ser. No. 918,819, Oct. 14, 1986, abandoned.

[51] Int. Cl.⁵ .............................................. A61K 31/74
[52] U.S. Cl. ................................. 424/78.02; 424/441; 424/448; 424/449
[58] Field of Search ............... 424/445, 447, 448, 449, 424/78.02

[56] References Cited

U.S. PATENT DOCUMENTS

| | | | |
|---|---|---|---|
| 3,964,482 | 6/1976 | Gerstel et al. | 604/890.1 |
| 4,031,894 | 6/1977 | Urquhart et al. | 188/59 |
| 4,161,527 | 7/1979 | Ishizuka et al. | 514/206 |
| 4,201,211 | 5/1980 | Chandrasekaran et al. | 424/448 |
| 4,230,105 | 10/1980 | Harwood | 128/156 |
| 4,241,057 | 12/1980 | Ishizuka et al. | 514/206 |
| 4,262,003 | 4/1981 | Urquhart et al. | 514/91 |
| 4,291,014 | 9/1981 | Keith et al. | 424/486 |
| 4,291,015 | 9/1981 | Keith et al. | 424/486 |
| 4,292,303 | 9/1981 | Keith et al. | 424/449 |
| 4,293,565 | 10/1981 | Cordes et al. | 514/470 |
| 4,336,243 | 6/1982 | Sanvordeker et al. | 424/449 |
| 4,346,709 | 8/1983 | Schmidt | 424/449 |
| 4,638,045 | 1/1987 | Kohn et al. | 424/78 |
| 4,957,744 | 9/1990 | della Valle et al. | 424/443 |

OTHER PUBLICATIONS

Kopecek and Ulbrich, Prog. Polym. Sci. 9:1-58 (1983).
Williams Engineering in Medicine 10:5-7 (1981).
Williams and Mort, Journal of Bioengineering 1:231-238 (1977).
Langer, Tech. Rev. pp. 26-34 (1981).
Maulding, et al., J. Controlled Release, 3:103-117 (1986).
Abrams, Z. Kardiol., 74(4):10-15 (1985).
Chien, Pharm. Technol., 50-66 (1985).
Heller, J. Controlled Release, 2:167-77 (1985).
Pitt, et al., J. Controlled Release, 2:363-374 (1985).
Keshary and Chien, Drug Devel. and Indus. Phrm., 10:833-913.
Pitt, et al., J. Controlled Release, 1:3-14 (1984).
Jarrett, et al., Polymers as Biomaterials, pp. 181-192 (1984).
Good, Drug Dev. & Industrial Pharm., 9:647-670 (1983).
Keith, Drug Dev. & Industrial Pharm., 9:605-625 (1983).
Williams, J. Materials Science, 17:1233-1246 (1982).
Chu, J. Applied Polymer Science, 26:1727-1734 (1981).

(List continued on next page.)

Primary Examiner—Thurman K. Page
Assistant Examiner—Leon R. Horne
Attorney, Agent, or Firm—Arnold, White & Durkee

[57] ABSTRACT

The present invention relates to a composition of matter for the time-dependent liberation of therapeutic agents. This composition of matter comprises a polymeric slab and a homogeneously dispersed enzyme which degrades the polymeric slab in the presence of moisture. The therapeutic agent is physically entrapped in the polymeric slab by inclusion during polymerization to form the polymeric slab or by mixture of the therapeutic agent with a liquid form of the polymeric slab and conversion of the liquid to a solid form. The therapeutic agent is not chemically bound to the polymer, and thus release of the agent is immediately effected upon the specific moisture-activated enzymatic degradation of the polymer slab. Moisture for enzymatic activation is provided by the biological surface on which the slab is emplaced, such as the dermal surface. The composition comprises a polymer such as poly (DL-lactide) and an enzyme such as proteinase K together with chlorpheniramine maleate as the therapeutic agent.

18 Claims, 19 Drawing Sheets

OTHER PUBLICATIONS

Dickinson, et al., J. Biomedical Materials Research, 15:577–589 (1981).
Reed and Gilding, Polymer, 22:494–498 (1981).
Langer, Chem. Eng. Commun., 6:1–48 (1980).
Williams, J. Biomedical Materials Research, 14:329–338 (1980).
Wood, Int. J. Pharmaceutics, 7:1–18 (1980).
Heller and Trescony, J. Pharm. Sciences, 68:919–921 (1979).
Moiseev, et al., J. Polymer Science, 66:269–276 (1979).
Pitt, et al., J. Pharm. Sciences, 68:1534–1538 (1979).
Williams, Corrosion and Degradation of Implant Materials, pp. 60–75 (1979).
Schindler, et al., Contemporary Topics in Polymer Science, pp. 1–286 (1977).
Langer and Peppas, Biomaterials, (1981).
Heller SRI International, Menlo Park, Calif. "Drug Release from Bioerodible Systems" (undated).

DELIVERY OF THERAPEUTIC AGENTS

The present application is a continuation-in-part of U.S. patent application Ser. No. 06/918,819, filed Oct. 14, 1986, now abandoned, upon which priority is claimed.

FIELD OF THE INVENTION

The present invention relates to the delivery of therapeutic agents and a system to control and enhance release of therapeutic agents from polymeric reservoirs. The unique utility of the present invention partially resides in the combination of a polymeric substance containing a therapeutic agent with a moisture-activated enzyme capable of degrading the polymeric substance to facilitate the liberation of the therapeutic agent.

BACKGROUND OF THE INVENTION

Polymeric materials have been used for medical and surgical applications for 30 to 40 years and these applications often involved the use of the polymers in intimate contact with living tissues (Williams, *Journal of Materials Science;* (1982), 17:1233–1246). It has been stated that "the development of polymers containing hydrolytically or enzymatically labile bonds has been an ongoing activity for a very long time, principally in connection with a search for improved absorbable sutures. Although these sutures were originally derived almost exclusively from various forms of collagen and evolved to the modern day catgut, there has also been an increasing emphasis on developing synthetic materials that would hydrolyze to natural metabolites.

As a result of these efforts, two materials emerged, poly(lactic acid) and poly(glycolic acid) (Heller, material presented at the Massachusetts Institute of Technology Special Summer Program held Jul. 19 through Jul. 23, 1982). Since the first disclosure of the use of a synthetic biodegradable polymer for the systemic delivery of a therapeutic agent reported by Yolles, et al. (1970), a large body of literature has evolved which describes therapeutic agent release from bioerodible polymers. Three types of therapeutic agent release have been described which can occur from bioerodible polymers based on the mechanism of polymer erosion. These three types are designated as Type I, Type II and Type III erosion.

A Type I erosion system is composed of a water-soluble polymer which has been insolubilized by hydrolytically unstable crosslinks. The three-dimensional network of the system remains intact (insoluble) and can only swell to the extent allowed by the crosslink density when first placed in an aqueous environment. However, on prolonged contact with an aqueous environment, the crosslinks, which are hydrolytically labile, begin to cleave, the crosslink density decreases and the network will swell to the point where the majority of the crosslinks are broken and the matrix will dissolve. This type of system is very useful for the release of agents which have a very low water solubility and for macromolecules that can be physically entangled in the matrix. In this last case, the agents cannot diffuse out even though they are very water soluble. As a result, escape and dissolution of the agents can only take place after enough crosslinks have been cleaved to allow disentanglement of the macromolecule.

A Type II erosion system is composed of water-insoluble polymeric material which can be solubilized by hydrolysis, ionization, or protonation of a pendant group. Since the solubilization does not involve backbone cleavage, there is no significant change in molecular weight of the polymer as it is solubilized. Due to this fact, this type of system is useful for topical applications where the elimination of high molecular weight, water-soluble macromolecules is not a problem. This is not the case where this type of system is used internally as implant material because, in this situation, high molecular weight materials can cause elimination problems. The major use of this type of system has been in the field of enteric coatings where these coatings are designed to be soluble at specific pH's of the gastrointestinal tract.

A Type III erosion system is composed of hydrophobic polymers which are converted to small, water-soluble molecules by cleavage of hydrolytically labile bonds in the polymer backbone. In the past, the principle use of this type of system has been for the systemic administration of therapeutic agents from subcutaneous, intramuscular, or intraperitoneal implantation sites where the method of therapeutic agent delivery necessitates the use of polymers whose degradation products are nontoxic. Heller (Heller, material presented at the Massachusetts Institute of Technology Special Summer Program held Jul. 19 through Jul. 23, 1982)) stated that systems based on this type of erosion are being developed along four parallel approaches. These include: (a) diffusional systems in which the rate-limiting barrier membrane will ultimately erode; (b) bioerodible microcapsules; (c) monolithic devices containing dispersed or dissolved therapeutic agent; and (d) bioerodible polymers containing therapeutic agents chemically bound to the polymer backbone.

This last class of bioerodable system was described by Kopachek et al. (1983, *Prog. Polym. Sci.,* 9:1–58) in an article reviewing the biodegradation of various biomedical polymers. The author reviews the work of others in the field who use polylactic acid as the polymer of choice. The rate of polymer degradation and drug release is controlled through chemical modification of the particular polymer(s) used as well as the ratio of included polymers one to another. However, the use of an extrinsic enzyme in or on the polymer device was not introduced to further control or enhance a linear rate of drug release from the polymer. While erosion rate modifiers, such as those disclosed by Schmidt et al. (U.S. Pat. No. 4,346,709), have been used in conjunction with polymeric devices to decrease the rate of drug delivery, the inclusion of a "modifier", for example an enzyme, has not been proposed to enhance the rate of drug release.

Others in the art have discussed the ability of naturally occurring enzymes to degrade polymeric substances (Williams, D. F. (1980), *Eng. Med.,* 10:5–7). For example, Williams described the enzymatic degradation of polylactic acid by various enzymes, including bromelain, esterase, ficin, lactate dehydrogenase, pronase and proteinase K (Id. at 6). However, the inclusion of a therapeutic agent in such a system was not addressed. The inclusion of a therapeutic agent in a polymeric substrate together with an enzyme was later examined by Langer and co-workers, but only in reference to the cleavage of drug-polymer bonds in a "pendant" chain system (Langer, A. (1980) *Chem. Eng. Commun.,* 6:1–48). This system required that the cleavage of the drug from the polymer backbone be the rate-limiting step in order that a constant release of the drug from the polymer be achieved (Id. at 33). Such would require that the rate of diffusion of the enzyme and the rate of diffusion of the drug be faster than the rate of drug-polymer cleavage by the enzyme (Id.). This particular system limited the use of therapeutic agents to those "bindable" ( i.e., those with particular conformational and/or structural characteristics) to a polymeric substrate. The use of enzymes in conjunction with unbound therapeutic agents in a polymeric slab, however, remained unexplored.

The present invention comprises a type III erosion system. However, the therapeutic agent of the present invention is not bound to the polymer backbone of the bioerodable polymer. In one well-characterized example, a monolithic system based on the use of poly(DL-lactide), a polymeric material that undergoes bulk degradation, is disclosed. The physically entrapped therapeutic agent included in the polymer is released as the enzyme is activated by moisture. The moisture-activated enzyme then degrades the polymeric slab, thus releasing the physically entrapped therapeutic agent. Release of the therapeutic agent is thus controlled by a combination of diffusion and erosion.

An objective of the present invention is to develop a slab of therapeutic agent-containing polymer which will release therapeutic agent at a relatively constant rate, the rate being affected by the enzymatic cleavage of the polymer by a preferred enzyme. The enzyme thus acts to internally control the physical release at a constant rate of unbound homogeneously-dispersed therapeutic agent from the polymeric structure in which it is contained.

As will be appreciated, the present invention is not taught or suggested by the art in general or the above described references. Particularly, the references do not address the specific inclusion of a moisture-activated enzyme in a polymeric device itself to enhance the rate of therapeutic drug delivery, such as the device described by Kopachek, Schmidt and Williams. While Langer et al. describes an enzyme and polymer-bound drug delivery system, the art is void of any suggestion or teaching of a polymeric device with a non-polymer bound therapeutic agent and moisture-activated enzyme. The present system thus is not limited to therapeutic agents with structural characteristics suitable for binding to a polymeric substrate, and further features a therapeutic agent release rate independent of the rate at which drug-polymer bonds are enzymatically cleaved. This limitation as described in regard to the device of Langer et al. has been overcome by Applicants' with a system which physically entraps the therapeutic agent, without polymer bonding, the polymeric structure of the device.

SUMMARY OF THE INVENTION

The present invention has amazingly been able to overcome the limitations existing in the polymeric devices of the past through the unique inclusion of both a non-polymer bound therapeutic agent and a moisture-activated enzyme homogeneously dispersed within the polymeric structure itself. The constant and enhanced rate of drug release characteristic of the claimed device has been accomplished through the physical entrapment of the drug within the matrices of the polymeric structure, rather than drug-polymeric bounding. Further, its unique moisture-activated enzyme system makes the device convenient for use on any dermal surface. The device's constant rate of drug release is attributable to its unique coordinated action of included ingredients, whereby moisture-activated, enzymatic-degradation of the slab facilitates the release of the unbound physically entrapped drug. A therapeutic agent is homogeneously dispersed in the polymeric substance by a variety of methods, for example by inclusion during polymerization to form the polymeric substance or mixture with a liquid polymeric substance and conversion of the liquid form to a solid form.

An important aspect of the present invention is the presence of a homogeneously-dispersed enzyme in the polymer capable of degrading the polymeric substance in the presence of moisture or water. This degradation facilitates release of therapeutic agents physically entrapped in the polymeric structure. The therapeutic agent is not to be chemically bound to the backbone of the polymeric structure. Thus, release of the therapeutic agent is not dependent upon the action of the enzyme to cleave polymer-therapeutic agent bonds. Additionally, the rate of drug release is not limited by the rate at which enzyme diffuses through the substrate, as the enzyme is homogeneously dispersed throughout the polymeric structure. One or more such enzymes may be included homogeneously dispersed within the polymeric substance itself as was the therapeutic agent above. An enzyme may also be situated or dispersed in proximity to a surface of the polymeric substance so that, when moisture is present, for example that usually on the skin, the enzyme is active and degrades the polymeric substance from its surface.

The present invention further includes a transdermal therapeutic agent-delivery device comprising a polymeric substance with an incorporated therapeutic agent. Also present in the transdermal therapeutic agent-delivery device is at least one enzyme homogeneously dispersed within the polymer which degrades the polymeric substance in the presence of moisture. The transdermal therapeutic agent-delivery device additionally comprises means for holding the device in contact with a biological surface, such as to the skin of humans or animals. Such means, by way of example, include bandaging tapes, elastic bands and adhesive surfaces.

Enzyme-degradable polymeric substances usable in the practice of the present invention are frequently in the general categories commonly known as polyesters, polyamides, polypeptides or polysaccharides. Certain typical enzyme-degradable polymeric substances have long been used as biodegradable materials for sutures, for example. These typical enzyme-degradable materials include polyesters of alkylhydroxylic acids including, for example, the polyesters of monomeric units such as lactic acid, glycolic acid, hydroxypropionic acid, hydroxybutyric acid and combinations thereof. Lactic acid and glycolic acid are most commonly used for this purpose. Other enzyme-degradable polymers well-known in the field include polymeric substances such as cellulose, dextran, elastin, fibrin, gelatin, polyethylene, pectin or polygalacturonic acid.

Enzymes usable in the practice of the present invention are of a wide variety but most frequently are proteases or hydrolases with ester-hydrolyzing capabilities. Particularly preferred enzymes include proteinase K, bromelain, pronase E, cellulase, dextranase, elastase, plasmin, streptokinase, trypsin, chymotrypsin, papain, chymopapain, collagenase, trypsin, subtilisn, clostridopeptidase A, ficin, carboxypeptidase A, pectinase, pectinesterase, an oxidoreductase or an oxidase. The most preferred enzymes include proteinase K, bromelain and pronase E. The enzymes of the present invention are homogeneously incorporated in the polymeric substance.

Therapeutic agents useful in the practice of the present invention are of a wide variety but most frequently are antiparasitic, motion-sickness preparations, hormonal agents, diuretics and the like. These agents are physically entrapped in a homogeneous dispersion within the polymeric substance and are included in therapeutically effective amounts. For purposes of this application, a therapeutically effective amount is a quantity of therapeutic agent which elicits a physiologically beneficial effect. A pharmacologically acceptable material as used in this application comprises a material which is non-toxic to living organisms.

The most preferred embodiment of the present invention comprises a poly(DL-lactide) polymeric slab, proteinase K enzyme at about 0.5% by weight of the slab and the therapeutic agent chlorpheniramine maleate. The present invention also features a method of transdermal drug delivery, in which the described polymeric structure is employed together with a means for attaching the structure to a biological surface, such as a patient's skin.

The polymeric substance of the transdermal therapeutic agent-delivery device is characterized as having a surface for skin contact. The enzyme may be dispersed on said surface or homogeneously dispersed in the polymeric substance itself. The transdermal therapeutic agent-delivery device of the present invention is also useful for topical treatment of cutaneous lesions.

DESCRIPTION OF THE PREFERRED EMBODIMENT

Figure 1:
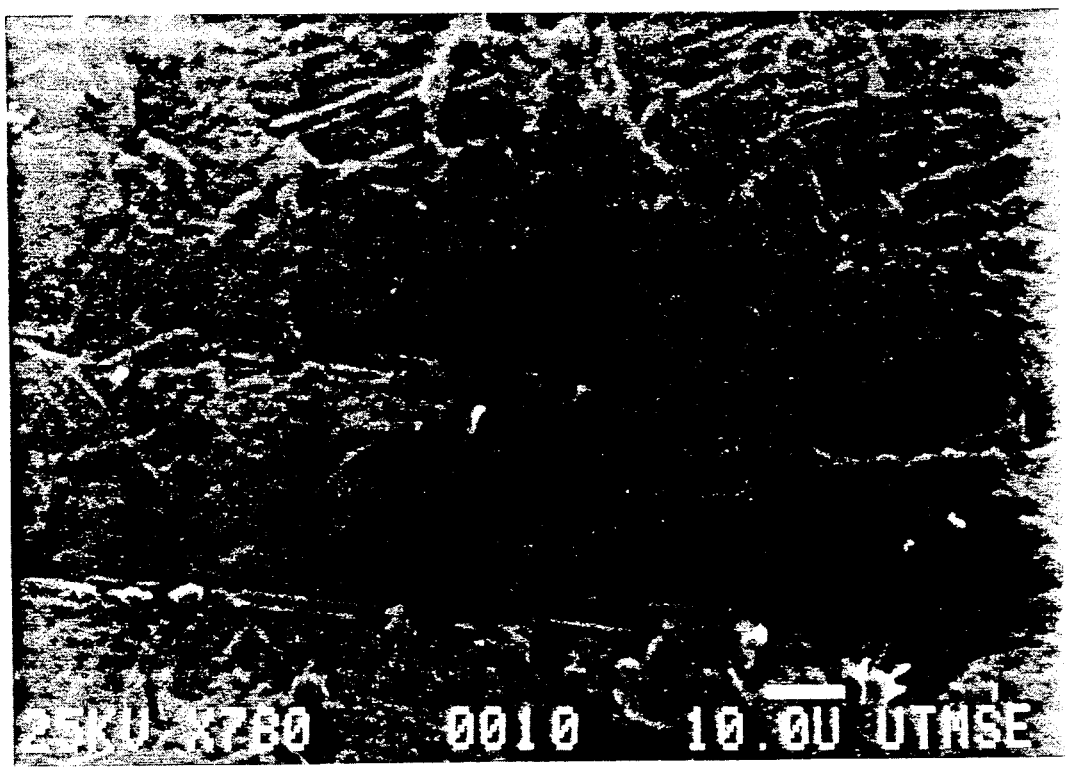
FIG. 1 shows 10% chlorpheniramine maleate and 90% poly(DL-lactide) 1.23 dL/g which was not exposed to any buffer.

In the specification and the accompanying claims, the term "therapeutic agent" broadly includes physiologically or pharmacologically active substances producing a general or localized systemic effect in mammals including humans and primates; avians; valuable domestic household, sport or farm animals; or for administering to laboratory animals such as mice, rats, guinea pigs; and the like. That is, the novel therapeutic agent delivery device can be used for administering therapeutic agents that are physiologically or pharmacologically active at a point in near relation to the therapeutic agent delivery device, or, for administering a systemically active substance which will produce a physiological or pharmacological response at a site remote from the point of application of the therapeutic agent delivery device.

The therapeutic agents that can be administered by the claimed device include, without limitation, for example, therapeutic agents acting on the central nervous system such as, hypnotics and sedatives such as pentobarbital sodium, phenobarbital, secobarbital, thiopental, etc; heterocyclic hypnotics such as dioxopiperidines, and glutarimides; hypnotics and sedatives such as amides and ureas exemplified by diethylisovaleramide an alpha-bromoisovaleryl urea and the like; hypnotics and sedative alcohols such as carbomal, naphthoxyethanol, methylparaphenol and the like; and hypnotic and sedative urethans, disulfanes and the like; psychic energizers such as isocarboxazid, nialamide, phenelzine, imipramine, tranylcypromine, pargylene and the like; tranquilizers such as chloropromazine, promazine, fluphenazine reserpine, deserpidine, meprobamate, benzodiazepines such as chlordiazepoxide, and the like; anticonvulsants such as primidone, diphenylhydantoin, ethotoin, pheneturide, ethosuximide and the like; muscle relaxants and anti-parkinson agents such as mephenesin, methocarbomal, trihexylphenidyl, biperiden, levo-dopa, also known as L-dopa and L-alpha-3-4 dihydroxyphenylalanine, and the like; analgesics such as morphine, codeine, meperidine, nalorphine and the like; antipyretics and anti-inflammatory agents such as aspirin, salicylamide, sodium salicylamide and the like; local anesthetics such as procaine, lidocaine, naepaine, piperocaine, tetracaine, dibucaine and the like; antispasmodics and antiulcer agents such as atropine, scopolamine, methscopolamine, oxyphenonium, papaverine, prostaglandins such as $PGE_1$, $PGE_2$, $PGF_{1a}$, $PGF_{2a}$, PGA and the like; anti-microbials such as penicillin, tetracycline, oxytetracycline, chlorotetracycline, chloramphenicol, sulfonamides and the like; antimalarials such as 4-aminoquinolines, 8-aminoquinolines and pyrimethamine; hormonal agents such as prednisolone, hydrocortisone, cortisol and triamcinolone; androgenic steroids, for example, methyltestosterone, fluoximesterone and the like; estrogenic steroids, for example, 17B-estradiol and ethinyl estradiol; progestational steroids, for example 17a-hydroxyprogesterone acetate, 19-nor-progesterone, norethindrone and the like; sympathemimetic therapeutic agents such as amphetamine, ephinephrine, epinephrine and the like; cardiovascular therapeutic agents, for example, procainamide, amyl nitrite, nitroglycerin, dipyridamole, sodium nitrate, isosorbide dinitrate and the like; diuretics, for example, chlorothiazide, flumethiazide and the like; antiparasitic agents such as bephenium hydroxynaphthoate and dichlorophen, dapsone and the like; anti-neoplastic agents such as mechlorethamine, adriamycin, methotrexate, uracil mustard, 5-fluorouracil, 6-thioguanine, procarbazine and the like; hypoglycemic therapeutic agents such as insulins, protamine zinc insulin suspension, globin zinc insulin, isophane insulin suspension, and other art known extended insulin suspensions, sulfonylureas such as tolbutamide, acetohexamide, tolazamide, and chlorpropamide, the biguanides and the like; nutritional agents such as vitamins, essential amino acids, essential fats and the like; and other physiologically or pharmacologically active agents.

Also, the therapeutic agents can be present as the pharmacologically acceptable derivatives, such as ethers, esters, amides, acetals, etc. that lend themselves to passage into the circulatory system. These derivatives can be prepared by art known techniques and then used in the practice of the invention. Of course, the therapeutic agent derivative should be such as to convert to the active therapeutic agent within the body through the action of body enzyme-assisted transformation, pH, specific organ activities, and the like. When a proteolytic enzyme is comprised by the device or composition of the present invention, polypeptide agents which are degraded by the enzyme should be avoided.

The amount of therapeutic agent present in the polymeric substance is a therapeutically effective amount, which is generally non-limited and is an amount equal to or larger than the amount of a therapeutic agent that, on its release from the polymeric substance, is effective for bringing about a desired physiological or pharmacological effects. For example, the amount of therapeutic agent present in the polymeric substance of a therapeutic agent-delivery device should be suitable for maintaining a supply of therapeutic agent when the device is used for a period of time to achieve local or systemic effects. For various therapeutic agents, such as 11-desmethoxyreserpine about 5 to 40 mg in the polymeric substance, may be suitable. For acetophenazine a suitable amount in the polymeric substance should be from 100 to 200 mg.

It will be appreciated by those versed in the art that the unique therapeutic agent delivery device of this invention can provide for the programmed delivery of therapeutic agent at a rate of delivery characterized by a zero order time dependence for prolonged periods of time; and, that the device therefore lends itself to administering an effective amount of therapeutic agent needed for a therapeutic effect while essentially avoiding the presence of excessive amount of therapeutic agent at the needed biological site. For example, the amount of therapeutic agent in the polymeric substance can be 10 to 30 mg of thiopropazate for releasing 5 to 10 mg over a given time; 100 to 200 mg in the polymeric substance of phenyltoloxamine for a release of 50 mg; 100 to 200 mg of papaverine in the polymeric substance for a release of 30 to 75 mg over a determined time; 500 to 600 mg of mephenoxalone for a release of 375 to 425 mg.

The present invention involves a device comprising a biodegradable polymeric slab preferably containing a therapeutic agent, a plasticizer and an enzyme. Such a device may be used for the slow release or transdermal delivery of the therapeutic agent. Bioerodible polymers such as DL-polylactic acid and polyglycolic acid have been used for many years in absorbable sutures. The most preferred embodiment of the present invention comprises a polymeric slab of poly (DL-lactide), the enzyme proteinase K, and the therapeutic agent chloropheniramine maleate. Most preferably, the concentration of proteinase K is about 0.5% by weight of the polymeric slab.

During the past fifteen years, systemic delivery of therapeutic agents by means such as therapeutic agents dispersed in biodegradable microspheres or pellets for implantation, has been reported. The polymers are hydrolyzed slowly over a period of weeks to several months to release the active component. The polymer degrades extremely slowly in water and without the presence of the enzyme in the polymer, topical therapeutic agent release from the polymeric slab would be overly slow. The inclusion of a plasticizer in the polymeric substance of the present device adds elasticity to the membrane so that it may follow the contours of the skin surface to which it is applied.

Drug release from the polymeric substance of the present invention is triggered by the enzymatic hydrolysis of the polymer that occurs in the presence of water or in the presence of the moisture in the surface layers of the skin. As the polymer (e.g., DL-polylactic acid) degrades to a monomer (lactic acid), the physically entrapped therapeutic agent is released from the slab and is available for percutaneous absorption through the skin. Most experience to date has been with a model monolithic system based on the use of poly (DL-lactide) which undergoes bulk degradation. This means that therapeutic agent release is controlled by a combination of diffusion and erosion. The enzymatic cleavage of the ester backbone of the polymer may be conducted with appropriate degradative enzymes. Studies have thus far found the enzyme proteinase K to have the most pronounced physical effect on the degradation of poly(DL-lactide) compared to other enzymes studied.

Since the polymers may be applied internally or to the surface of the skin, pharmacologically acceptable biocompatible polymers are preferred for the present invention. These include polymers that might not normally be injected or implanted into the body since they would not be broken down to readily metabolizable monomers. Usable polymers may include, for example, cellulose, dextran, elastin, fibrin, gelatin, polyethylene, polyesters and polyamides. All of these polymers may undergo enzymatic degradation to monomers that are harmless or inactive to the skin surface or other biological structures.

The composition of the present invention may also be used for the internal emission of therapeutic agents. This internal emission of therapeutic agents may, for example, be in the digestive tract, the muscle or in proximity to a joint. Administration of the enzyme and therapeutic agent-containing polymeric substance of the present invention would respectively be by ingestion, intramuscular insertion or intraarticular insertion. Ingestion would lead to release of the therapeutic substance in the intestinal system when incorporated enzyme degrades the polymeric substance.

With intramuscular or intraarticular insertion, for example by injection of emulsification-produced particles having a size of less than 50 microns, the therapeutic agent would be released as the polymeric substance was degraded to metabolizable or excretable monomeric units. The composition of the present invention could also be internally utilized as larger pieces which were enzymically dissolved as therapeutic agent was exhausted. Such internal uses could be therapeutically or prophylactically used with humans or with animals. When cattle, for example, are treated with an implanted composition, the composition may be prepared to be totally degraded by the time the cattle are slaughtered for consumption.

Present marketed dosage forms utilize two mechanisms for controlling therapeutic agent release from a transdermal therapeutic agent-delivery system. The first and most popular method is the membrane diffusion controlled system. The other two systems that are on the market involve therapeutic agent release from a polymeric matrix. In these systems, very small quantities of therapeutic agent are released from the matrix. One major problem with matrix systems is that small quantities of therapeutic agent are released and in many cases the system essentially shuts off and does not release adequate amounts of further medication. The present biodegradable system circumvents these problems. Preliminary studies have shown that release rates are constant and very dependent on the level of enzyme in the slab or film of the present invention. For example, data presented at FIG. 17 demonstrates the increase in release of the therapeutic agent chlorpheniramine maleate as a function of increasing concentrations of the enzyme proteinase K in the polymeric slab.

The present transdermal systems require the presence of moisture on an occluded surface to trigger therapeutic agent release from the device. More specifically, accumulation of moisture on the biological surface activates the enzyme to degrade the polymeric slab, thereby releasing the therapeutic agent physically entrapped in the polymeric device.

Where the enzyme is not compatible with the organic solvent that would be used to cast these slabs, the enzyme could be applied to the outer surface of the slab in sufficient quantities to trigger polymeric degradation while the device is present on the skin. Since the matrix system generally has limitations for many therapeutic agents, there are presently few alternatives to membrane diffusion control systems.

The device of the present invention should also have applications in the animal health area for the topical delivery of therapeutic agents to the skin surface for a wide variety of animals. There could also be some potential applications in flea and tick collars where an insecticide would be released by the triggering action of the water and enzyme causing erosion of the polymer, as described above.

Table 1 shows many compatible combinations of polymeric materials and degradative enzymes useful or potentially useful in the practice of the present invention.

TABLE 1

| Polymer | Enzyme(s) | Monomers(s) |
| --- | --- | --- |
| 1. Cellulose | Cellulase | Hexose Sugars |
| 2. Dextran | Dextranase | Glucose(primarily) |
| 3. Elastin | Elastase | Peptides(? |
| 4. Fibrin | Plasmin | Short Polypeptides |
|  | Streptokinase | Short Polypeptides |
|  | Trypsin, | Short Polypeptides |
|  | Chymotrypsin | Short Polypeptides |
|  | Papain, | Short Polypeptides |
|  | Chymopapain | Short Polypeptides |
| 5. Gelatin | Collagenase | Peptides |
|  | Trypsin | Peptides |
|  | Chymotrypsin | Peptides |
|  | Papain, | Peptides |
|  | Chymopapain | Peptides |
| 6. Polyamides | Chymotrypsin |  |
| 7. Poly-(amino acids) (e.g. poly-lysine, poly-glutamic acid) | Trypsin Chymotrypsin Elastase Subtilisin | Short Polypeptides |
| 8. Polyethylene | Oxidoreductase Oxidase |  |
| 9. Pure Polygalacturonic acid or Crude Pectin | Pectinase or Pectinesterase | Galacturonic Acid |
| 10. Poly(hydroxy-alkyl acids) e.g.-poly-lactic acid, polyglycolic acid | Carboxypeptidase A chymotrypsin Ficin Proteinase K Bromelain Pronase E | Short Acid Chains and hydroxy Acids |

A preferred enzyme usable in the practice of the present invention is the fairly nonspecific protease, proteinase K. This enzyme is active even under extreme conditions which include: (a) high temperature-reported to be 12 times more active at 65° C. than at 25° C.; (b) extreme pH-active at pH 4 through pH 12.5. Preliminary work with this and a number of other enzymes has indicated that proteinase K has a pronounced physical effect of degradation on poly(DL-lactide).

A particular model system presently developed involves a slab comprising poly(DL-lactide), the enzyme proteinase K, and chlorpheniramine maleate as the model therapeutic agent. These devices were fabricated by dissolving therapeutic agent and poly(DL-lactide) in methylene chloride, suitably dispersing proteinase K in the solution (when enzyme was added), casting the mixture on a mold, such as an aluminum surface, and then evaporating the solvent at room temperature. The dissolution of the prepared slab is then carried out using a modified version of the USP Apparatus 2 Method of Dissolution. Samples of the dissolution media were taken periodically and assayed for chlorpheniramine maleate using UV spectrophotometry. This method allowed the release of the therapeutic agent in the presence and absence of the enzyme to be followed. In addition, the method of scanning electron microscopy (SEM) was used to physically observe the effect of the enzyme in the polymer slab.

Figure 17:
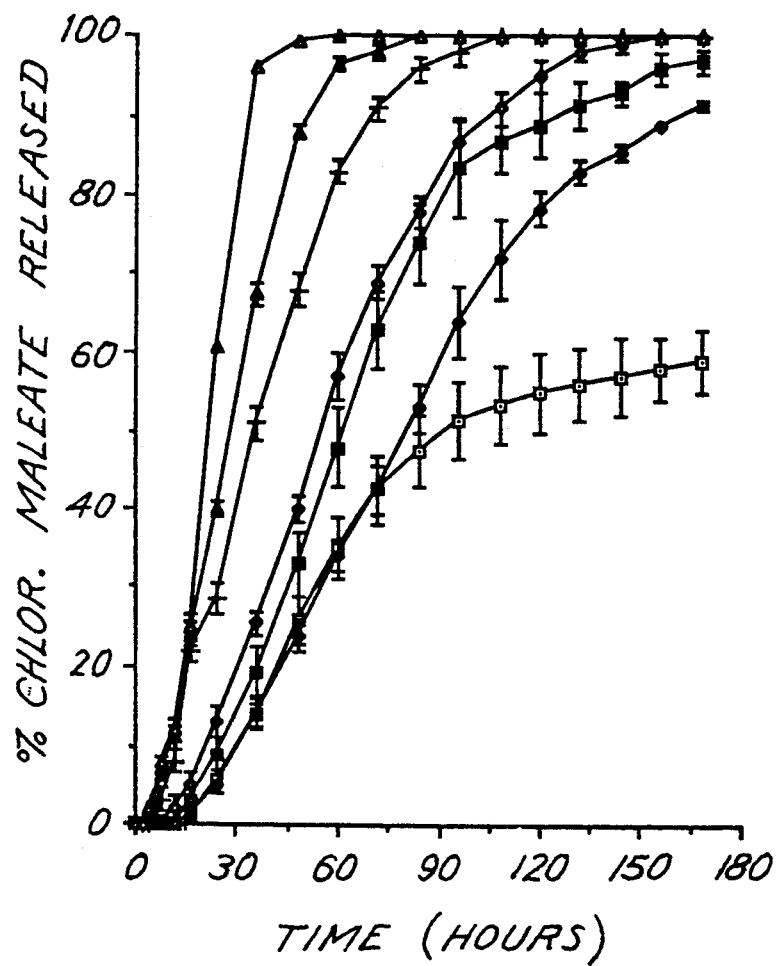
FIG. 17 shows the rate of drug release of chlorpheniramine maleate as a function of proteinase K enzyme concentration in the polymeric slab.

Assay results have shown that an increase in the enzyme concentration in the slab caused an increase in therapeutic agent release from the system. At one percent level of enzyme (as opposed to no enzyme) in the slab, a 6-fold increase in therapeutic agent release was found after a 24-hour dissolution study (FIG. 17). In addition, SEM results showed that slabs with enzyme exhibited major surface erosion after being subjected to the dissolution media for 24 hours. A slab containing 2% proteinase K showed a 12 fold increase in drug release after 24 hr.

These examples are presented to describe preferred embodiments and utilties of the present invention and are not meant to limit the present invention unless otherwise stated in the claims appended hereto.

EXAMPLE 1

Effect of Enzymes on Poly(DL-Lactide) Slabs Containing Model Therapeutic Agents

Materials and Methods for Slab Preparation—poly(DL-lactide) of inherent viscosity 1.23 dL/g was used in this test. Slabs were prepared by weighing a quantity of chlorpheniramine maleate (the model therapeutic agent) that would give 50 mg. of therapeutic agent per slab (10% w/w), dissolving the therapeutic agent in a small amount of methylene chloride in a beaker, adding a quantity of the poly(DL-lactide) 1.23 that would give 450 mg. of polymer per slab (90% w/w), and finally bringing the solution to a final volume that would allow 5 ml. of the therapeutic agent/polymer solution to contain 50 mg. of therapeutic agent and 450 mg. of polymer. After mixing well, 5 ml. quantities of the solution were cast into 4.4 cm. aluminum dishes. The slab-containing dishes were then placed on a laboratory benchtop, covered with aluminum foil, and left for a 24 hour period to allow the methylene chloride to evaporate. At the end of 24 hours, the slabs were placed in a desiccator with calcium sulfate until ready for the study.

Enzyme solution content—Tris 0.1M buffer solutions with pH's of 7.8 and 8.0 and a 0.1M phosphate, 50 mM EDTA, and 5 mM cysteine buffer with a pH of 7.4 were prepared. pH's were adjusted with concentrated HCl.

Figure 2:
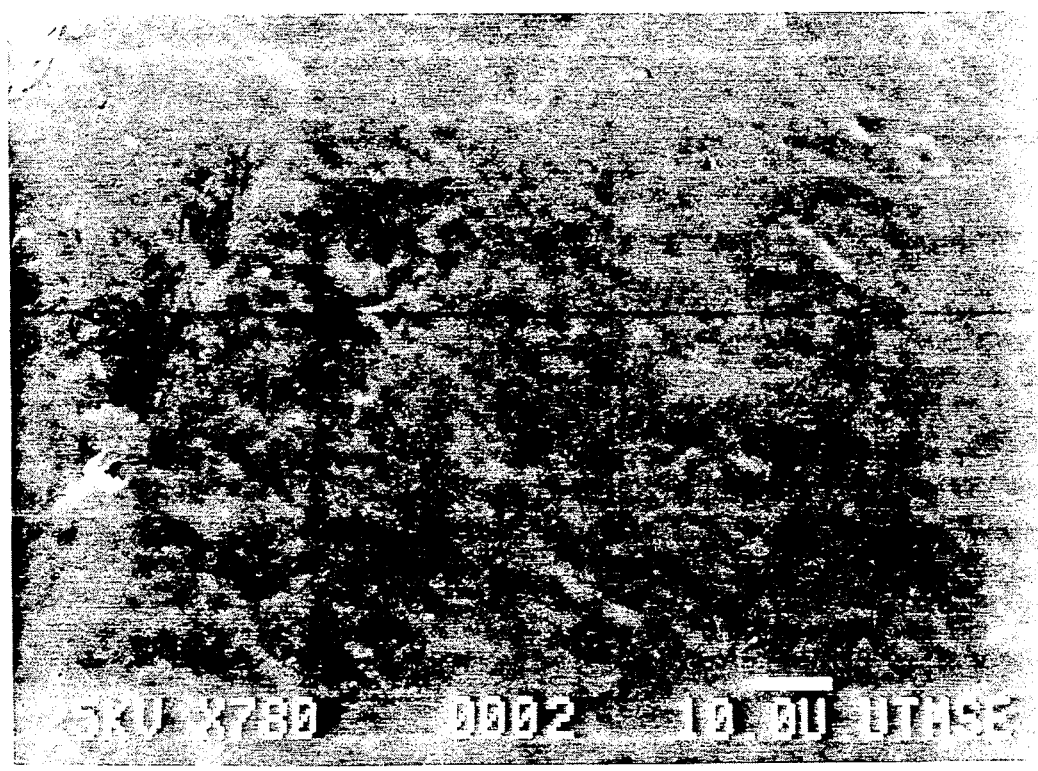
FIG. 2 shows 10% chlorpheniramine maleate and 90% poly(DL-lactide) 1.23 dL/g was exposed to 0.1M Tris buffer (pH=8.0) for 4 days (from vial #1).
Figure 3:
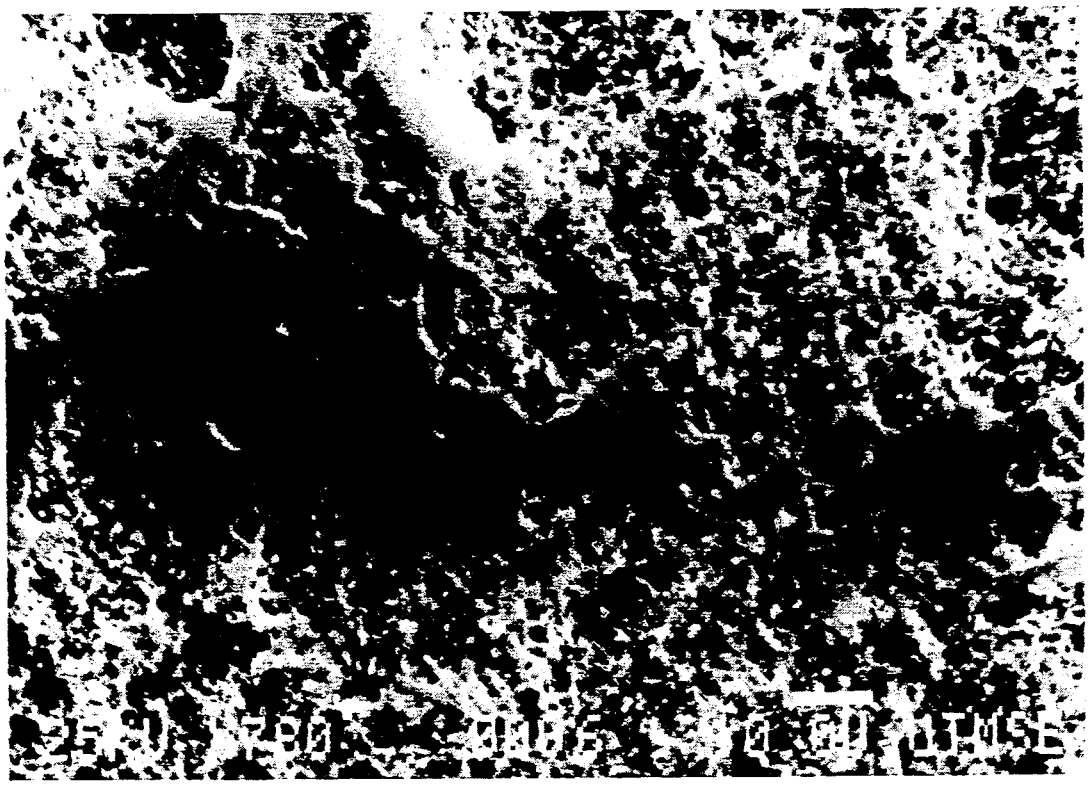
FIG. 3 shows 10% chlorpheniramine maleate and 90% poly(DL-lactide) 1.23 dL/g which was exposed to 0.1M Tris buffer (pH=8.0), containing 1 mg. of proteinase K, for 4 days (from vial #2).
Figure 4:
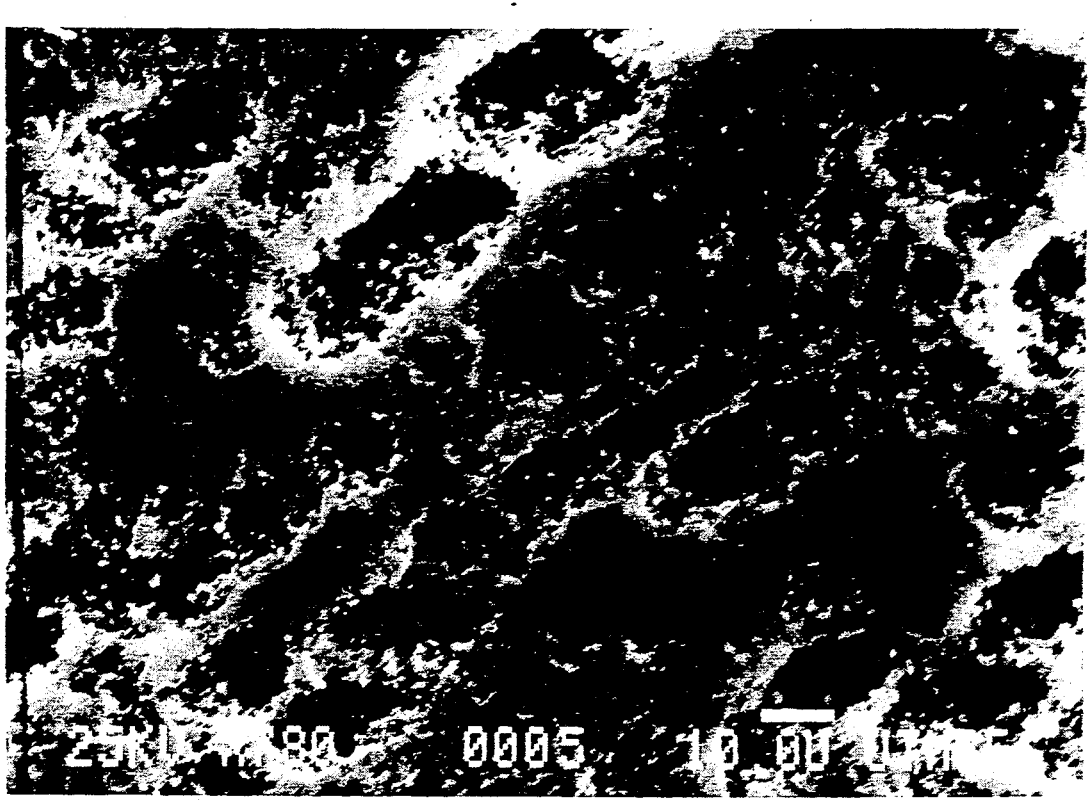
FIG. 4 shows 10% chlorpheniramine maleate and 90% poly(DL-lactide) 1.23 dL/g which was exposed to 0.1M Tris buffer (pH=8.0), containing 2 mg. of proteinase K, for 4 days (from vial #3).
Figure 5:
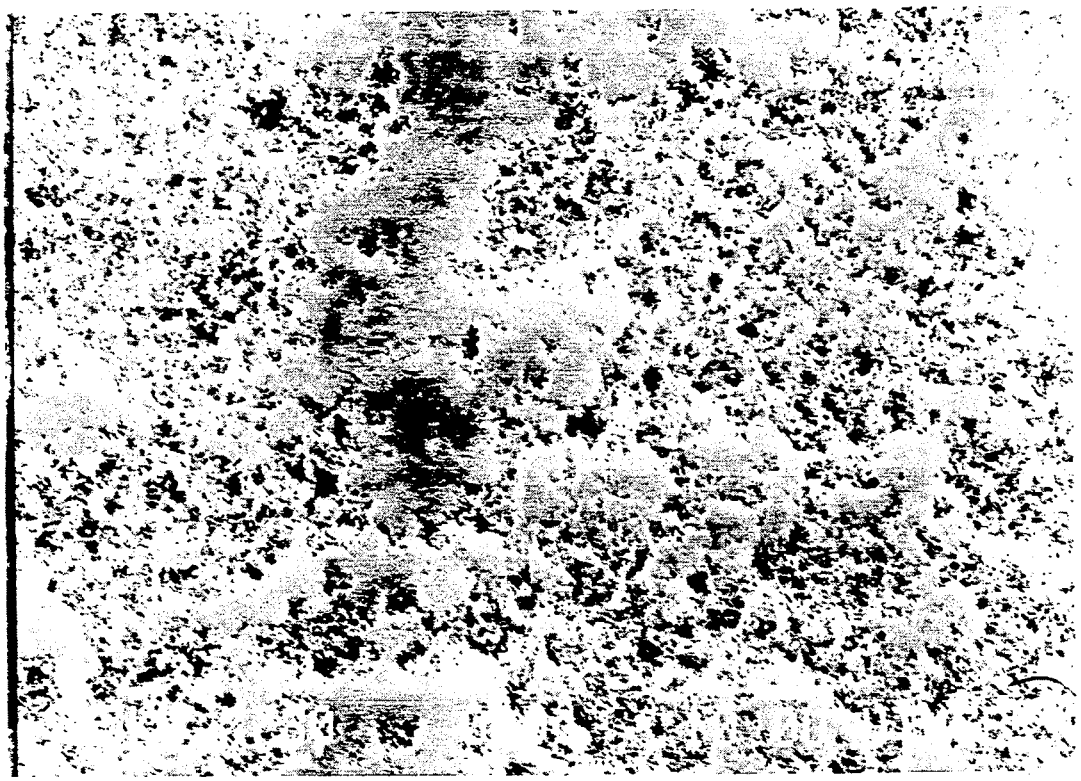
FIG. 5 shows 10% chlorpheniramine maleate and 90% poly(DL-lactide) 1.23 dL/g which was exposed to 0.1M Tris buffer (pH=8.0), containing 4 mg. of proteinase K, for 4 days (from vial #4).
Figure 6:
FIG. 6 shows 10% chlorpheniramine maleate and 90% poly(DL-lactide) 1.23 dL/g which was exposed to 0.1M Tris buffer (pH=7.8), containing 10 mg. of pronase E, for 4 days (from vial #6).
Figure 7:
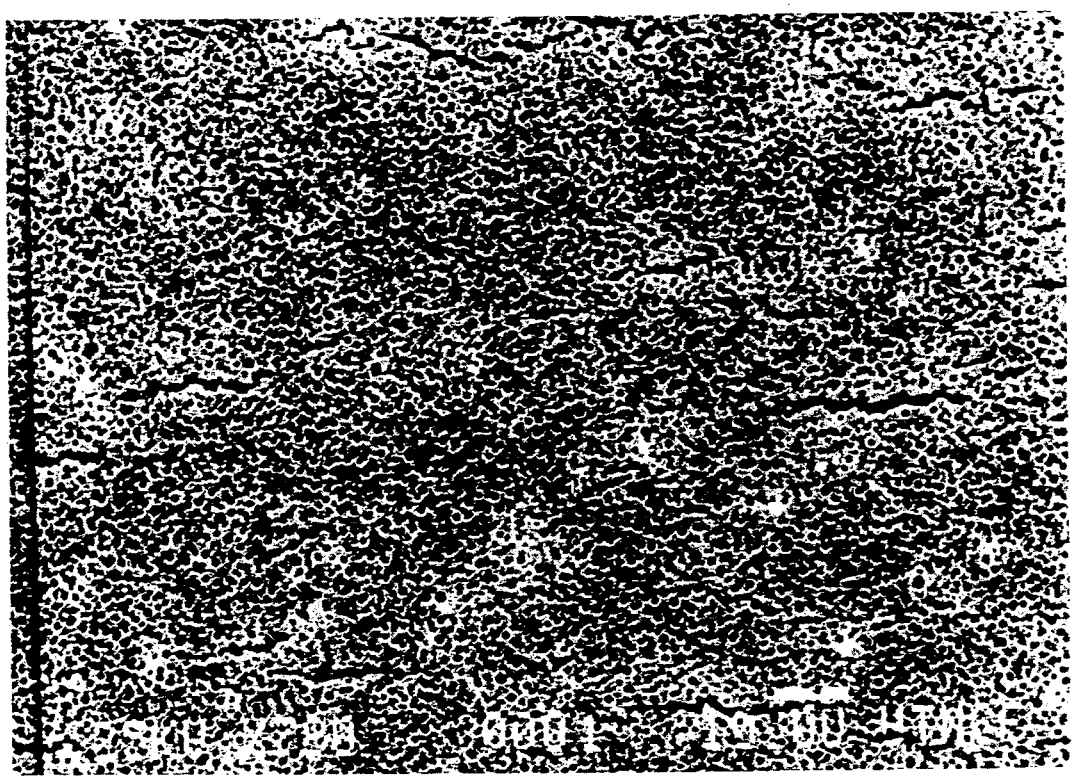
FIG. 7 shows 10% chlorpheniramine maleate and 90% poly(DL-lactide) 1.23 dL/g which was exposed to 0.1M Tris buffer (pH=7.8), containing 20 mg. of pronase E, for 4 days (from vial #7).
Figure 8:
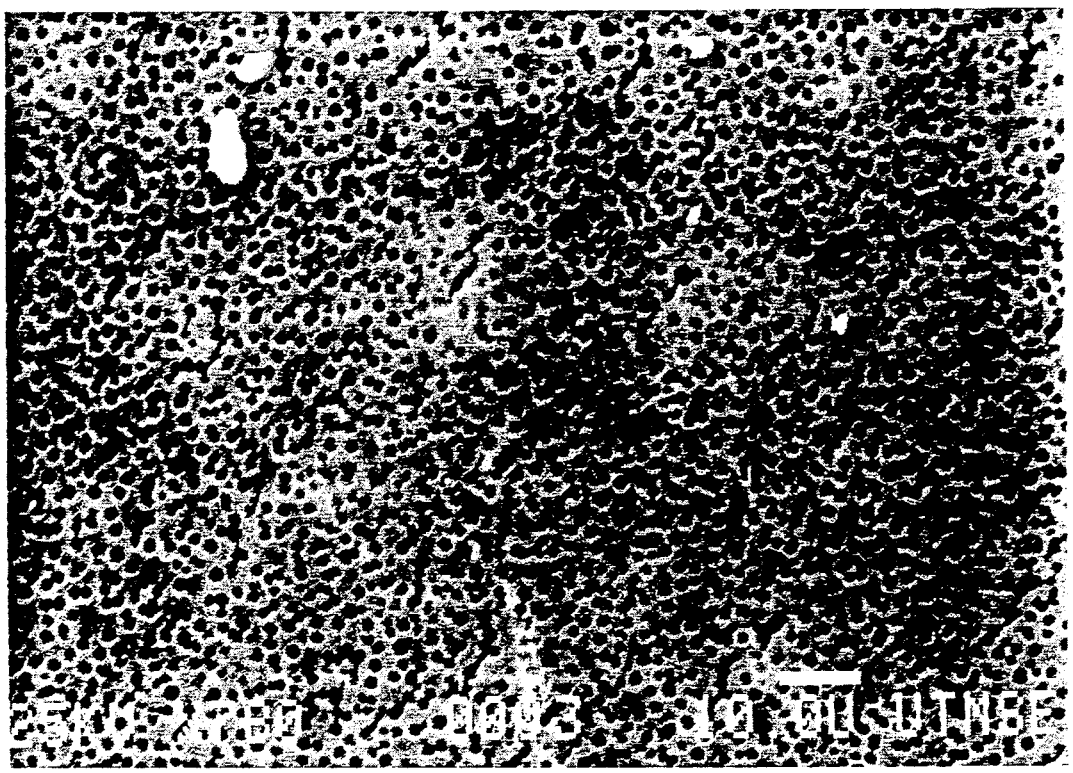
FIG. 8 shows 10% chlorpheniramine maleate and 90% poly(DL-lactide) 1.23 dL/g which was exposed to 0.1M Tris buffer (pH=7.8), containing 100 mg. of pronase E, for 4 days (from vial #9).
Figure 9:
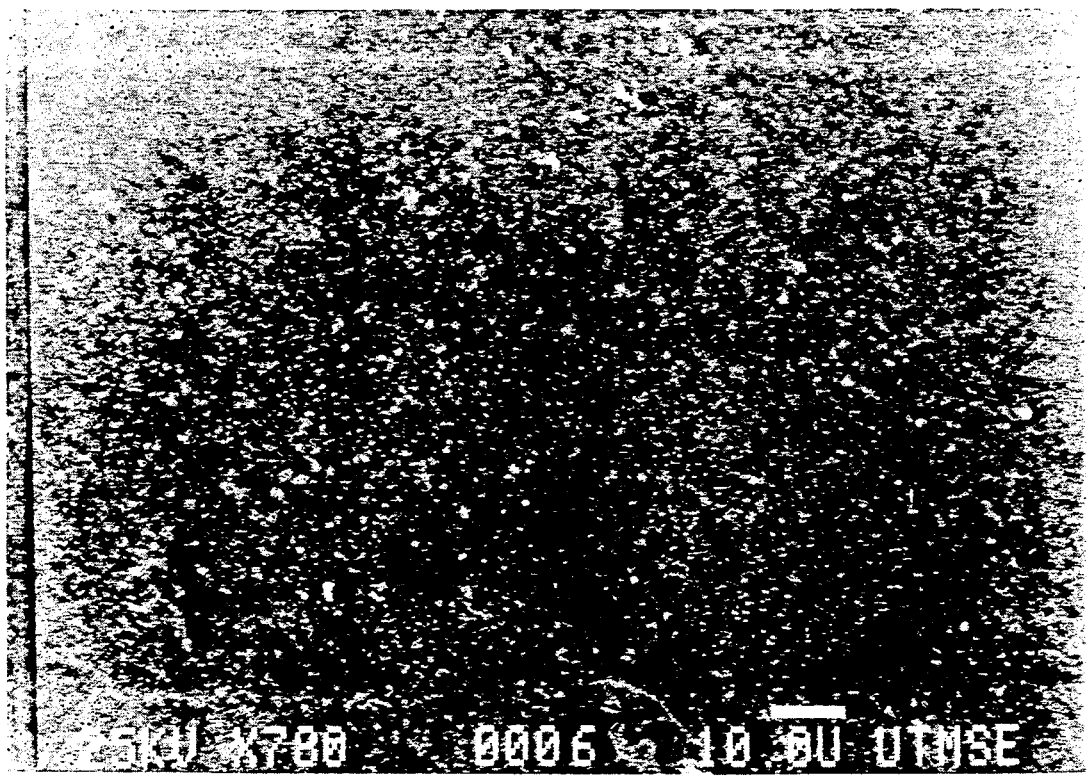
FIG. 9 shows 10% chlorpheniramine maleate and 90% poly(DL-lactide) 1.23 dL/g which was exposed to 0.1M Phosphate buffer (pH=7.4), containing 100 mg. of bromelain, for 4 days (from vial #11).
Figure 10:
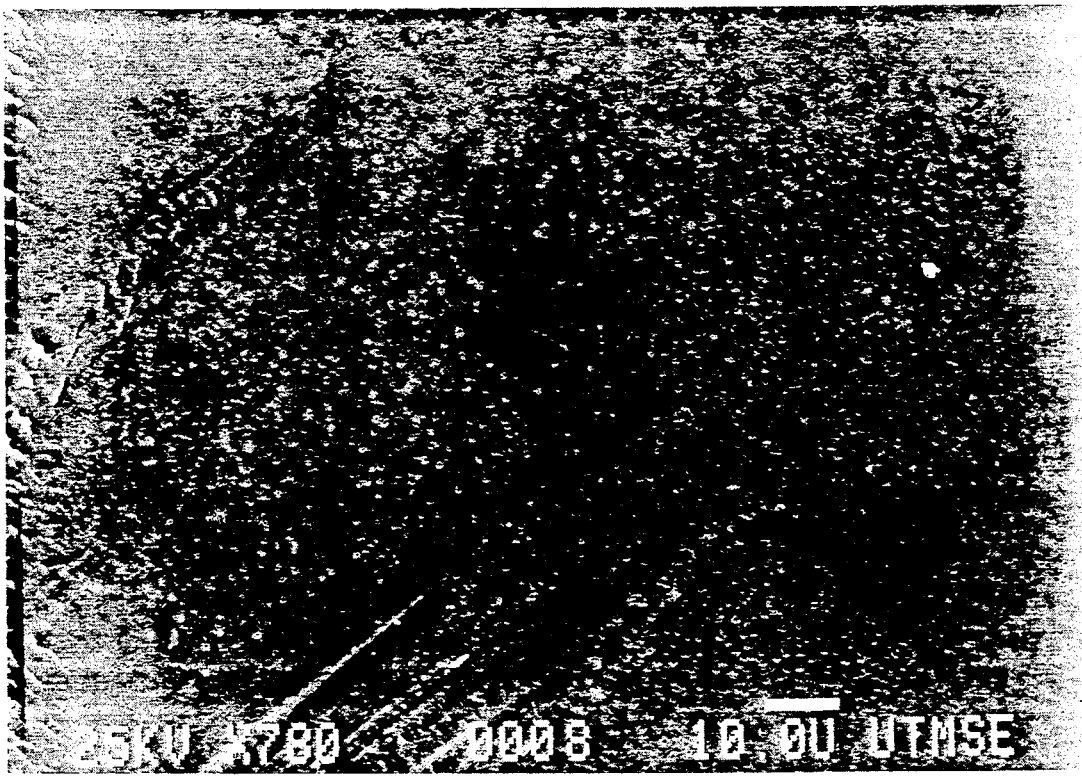
FIG. 10 shows 10% chlorpheniramine maleate and 90% poly(DL-lactide) 1.23 dL/g which was exposed to 0.1M Phosphate buffer (pH=7.4), containing 200 mg. of bromelain, for 4 days (from vial #12).
Figure 11:
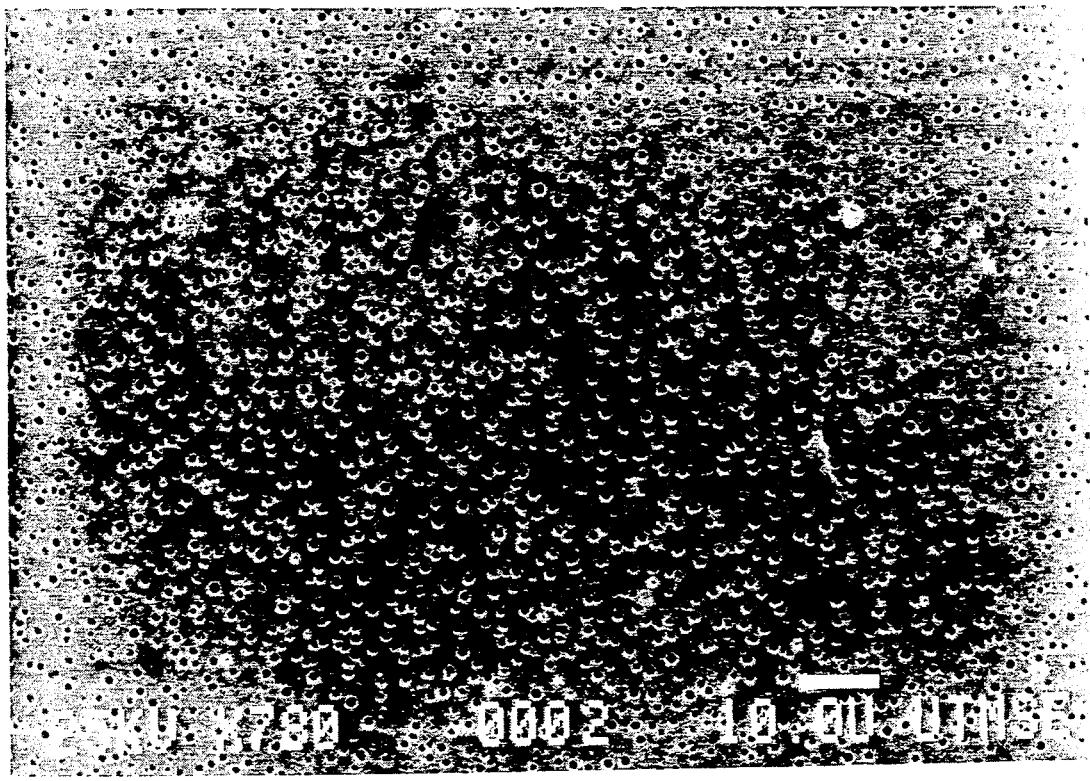
FIG. 11 shows 10% chlorpheniramine maleate and 90% poly(DL-lactide) 1.23 dL/g which was exposed to 0.1M Phosphate buffer (pH=7.4), containing 500 mg. of bromelain, for 4 days (from vial #13).

Test set-up and Results—2 small circles (approx. 2 cm. in diameter each) were cut from each slab (see FIG. 1). Each circular piece of slab was placed in a 20 ml. glass scintillation vial. Various solutions were then placed in each vial. The contents of the solutions placed in the vials were as follows:

| Vial # | Contents |
| --- | --- |
| 1 | 5 ml. of pH 8.0 Tris Buffer (see FIG. 2) |
| 2 | 5 ml. of pH 8.0 Tris Buffer + 1 mg. of proteinase K (see FIG. 3) |
| 3 | 5 ml. of pH 8.0 Tris Buffer + 2 mg. of proteinase K (see FIG. 4) |
| 4 | 5 ml. of pH 8.0 Tris Buffer + 4 mg. of proteinase K (see FIG. 5) |
| 5 | 5 ml. of pH 7.8 Tris Buffer |
| 6 | 5 ml. of pH 7.8 Tris Buffer + 10 mg. of pronase E (see FIG. 6) |
| 7 | 5 ml. of pH 7.8 Tris Buffer + 20 mg. of pronase E (see FIG. 7) |
| 8 | 5 ml. of pH 7.8 Tris Buffer + 30 mg. of pronase E |
| 9 | 5 ml. of pH 7.8 Tris Buffer + 100 mg. of pronase E (see FIG. 8) |
| 10 | 5 ml. of pH 7.4 Phosphate Buffer |
| 11 | 5 ml. of pH 7.4 Phosphate Buffer + 100 mg. of bromelain (see FIG. 9) |
| 12 | 5 ml. of pH 7.4 Phosphate Buffer + 200 mg. of bromelain (see FIG. 10) |
| 13 | 5 ml. of pH 7.4 Phosphate Buffer + 500 mg. of bromelain (see FIG. 11) |

Once all vials were prepared, they were incubated in a shaking water bath set at 32° C. All solutions were replaced very 24 hours to better ensure that an active enzyme was kept in contact with those samples containing enzyme solutions. The study was run for 4 days. At the end of 4 days, the condition of the slab samples was noted.

In all cases, the samples in contact with buffer solution showed no evidence of surface erosion. The samples in contact with the enzyme solutions had a dull surface evidencing erosion had occurred. Some of the samples were observed under a scanning electron microscope in order to observe the surface of the samples under high magnification. The scanning electron micrographs are shown in FIGS. 1–16.

EXAMPLE 2

Effect of Enzymes on Poly(DL-Lactide) Slabs Containing Model Therapeutic Agents

The same method of preparation of slabs was performed as described in Example 1 except that before casting the slab solution into aluminum dishes, a fine powder of the enzyme proteinase K was added to the solution so that a concentration of 1% w./w was obtained in the slab. As a result of this, the chlorpheniramine maleate concentration remained 10% w/w but the polymer concentration became 89% w/w. The suspension of the enzyme in the slab solution was then mixed by stirring. The slabs were then cast and evaporated as described in Example 1.

Poly(DL-lactide) with an inherent viscosity of 0.71 dL/g was used in this study.

Slabs were also prepared with 10% w/w chlorpheniramine maleate and 90% w/w poly(DL-lactide) 0.71 using the same procedure as noted for Example 1.

Dissolution Study Set-up and Results—The USP Apparatus 2 Method of Dissolution was used to check the release rate of both sets of slabs (with and without enzyme). The dissolution test methods were as follows:

Temperature—32°±0.5° C.
Speed of Paddles—30 rpm
Dissolution Media—0.01M Tris Buffer (pH 8.0)

Samples of the dissolution media were taken periodically and assayed for chlorpheniramine maleate using UV spectrophotometry. This allowed the release of the therapeutic agent in the presence and absence of the enzyme to be followed. Results of the UV assay, showed at the one per cent level of enzyme (as opposed to no enzyme) in the slab, a 5- to 6-fold increase in therapeutic agent release was found after a 24-hour dissolution study. In addition, scanning electron microscopy results showed that slabs with enzyme exhibited major surface erosion after being subjected to the dissolution media for 24 hours. Pictures of the scanning electron micrographs are attached at the end of this report. Please note that the enzyme used in this study had a reported activity of 17 U/mg. of protein (using casein as the substrate).

EXAMPLE 3

Effects of Plasticizers on Slab Formation

Plasticizers are preferred inclusions in the composition of the present invention. Numerous plasticizers are usable and known to those skilled in the art.

Particular plasticizers were mixed in slabs with poly(DL-lactide) 0.71 to determine which were most promising for formulation purposes.

The specific plasticizers used and their concentrations in the slabs were as follows:

| Plasticizer | % w/w in the Slab |
| --- | --- |
| 1. Triacetin | 10, 15, 20, & 30 |
| 2. Triethyl Citrate | 10, 15, 20, & 30 |
| 3. Dibutyl Phthalate | 10, 15, 20, & 30 |
| 4. Diethyl Phthalate | 10, 15, 20, & 30 |
| 5. Dioctyl Phthalate | 10, 15, 20, & 30 |
| 6. PVP K15 | 10, 15, 20 |
| 7. PVP K30 | 10, 15, 20 |
| 8. PVP K90 | 10, 15, 20 |

The slabs were prepared by weighing the amount of plasticizer needed to acquire the desired % w/w concentration (based on a final total slab weight of 500 mg.), then dissolving the plasticizer in 5 ml. of methylene chloride, adding the needed amount of poly(DL-lactide) 0.71 to reach a slab weight of 500 mg., and then casting the solution in a 4.4 cm. aluminum dish. All the dishes were covered with aluminum foil, evaporated 24 hours on the benchtop, and then put in a desiccator with anhydrous calcium sulfate until ready for observation.

1. Triacetin, triethyl citrate, dibutyl phthalate, and diethyl phthalate gave relatively clear, plastic slabs up to a concentration of 20% w/w. A concentration of 30% in each case produced a sticky slab at room temperature and humidity.

2. Dioctyl phthalate did not produce as desirable a slab as the other two phthalates used. In addition, this plasticizer produced a slightly sticky slab at a 20% w/w concentration whereas the others already mentioned did not.

3. Of the three PVP's (polyvinylpyrrolidones), PVP K90 produced the most homogeneous slabs (in appearance) even up to a concentration of 20% w/w.

EXAMPLE 4

Enzyme Dispersed on the Surface of a Polymeric Substance

A slab of 10% chlorpheniramine maleate and 90% poly(DL-lactide) 0.71 dL/g was prepared following the procedure described in Example 1. Once the slab was cast, the methylene chloride was allowed to evaporate until the slab just formed. Then, a suspension was made by adding 10 mg. of finely powdered proteinase K to a 2.5% solution of Klucel LF in methylene chloride. 2 ml of this suspension were pipetted onto the surface of the slab and spread evenly over the slab. The slab-containing dish was then covered with aluminum foil, left sitting on the benchtop for 24 hours, and then placed in a desiccator containing calcium sulfate until ready for observation.

Observation of slab—The slab had a smooth appearance and the enzyme was spread evenly over the surface of the slab.

EXAMPLE 5

Effect of Enzymes on Poly(DL-Lactide) Slabs Prepared from Lower Viscosity Poly(DL-Lactide)

Figure 12:
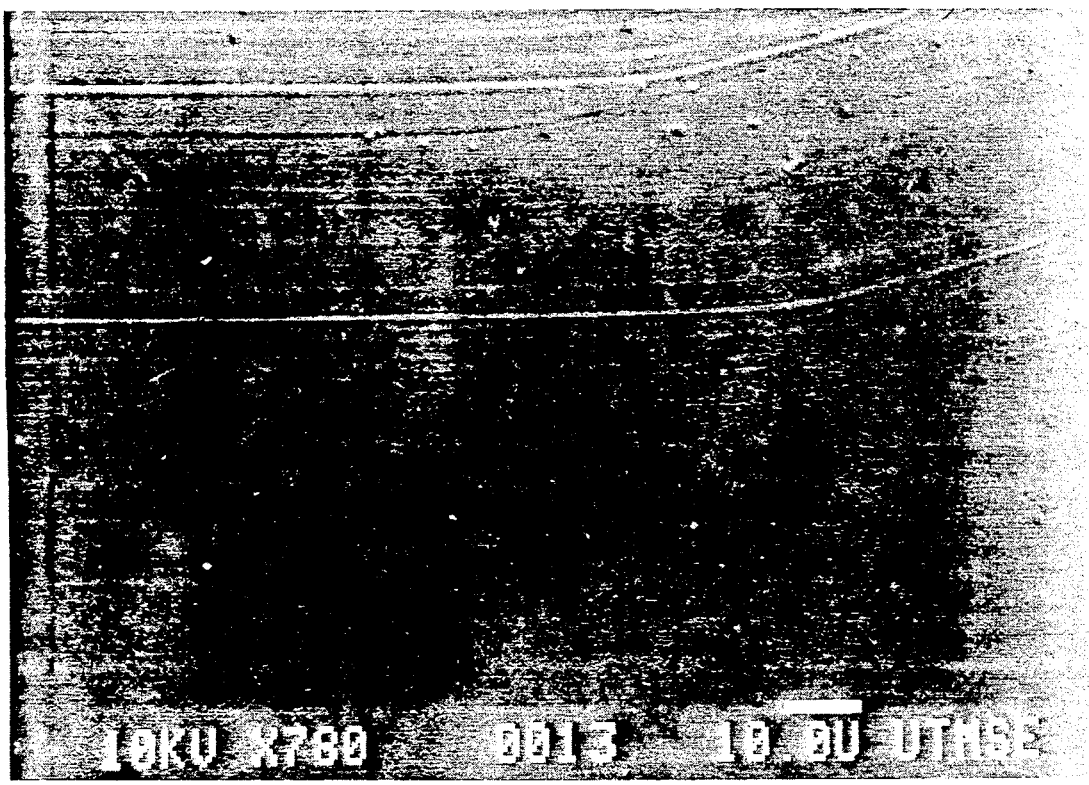
FIG. 12 shows 10% chlorpheniramine maleate and 90% poly(DL-lactide) 0.71 dL/g which was exposed to 0.1M Tris buffer (pH=8.0) for 24 hours.
Figure 13:
FIG. 13 shows 10% chlorpheniramine maleate and 90% poly(DL-lactide) 0.71 dL/g which was exposed to 0.1M Tris buffer (pH=8.0) for 24 hours—note: same slab as in FIG. 12—a different area of the slab.
Figure 14:
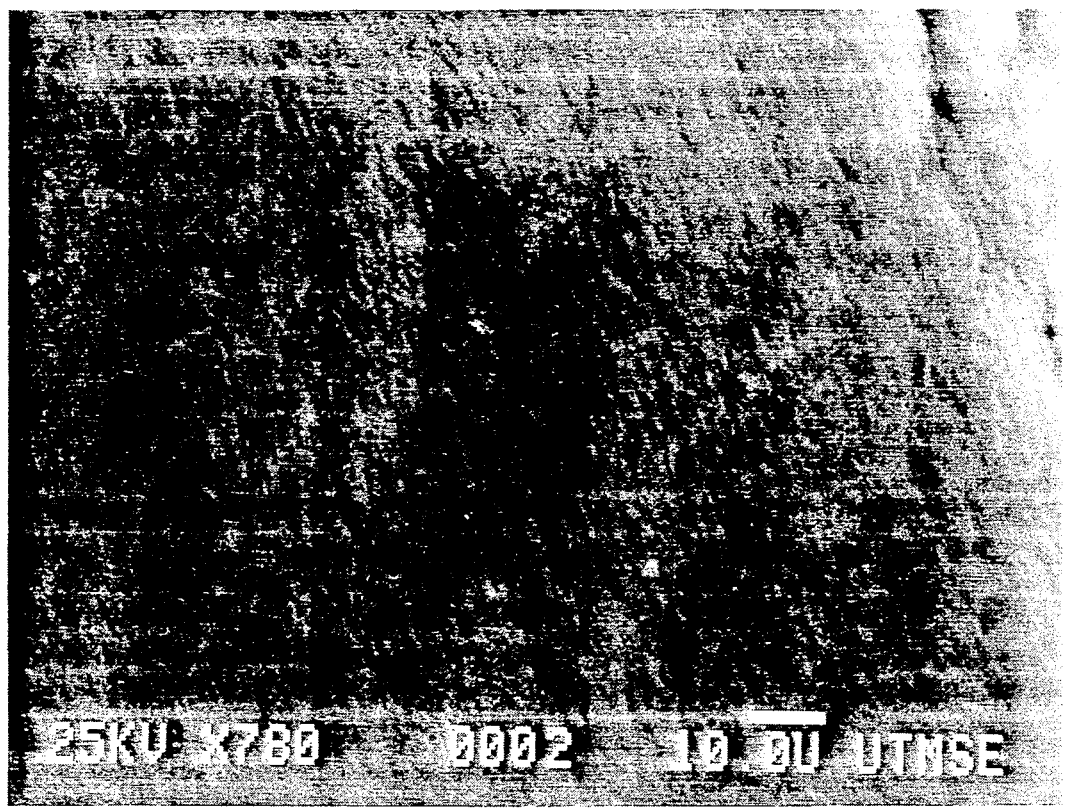
FIG. 14 shows 10% chlorpheniramine maleate and 90% poly(DL-lactide) 0.71 dL/g which was not exposed to any buffer.
Figure 15:
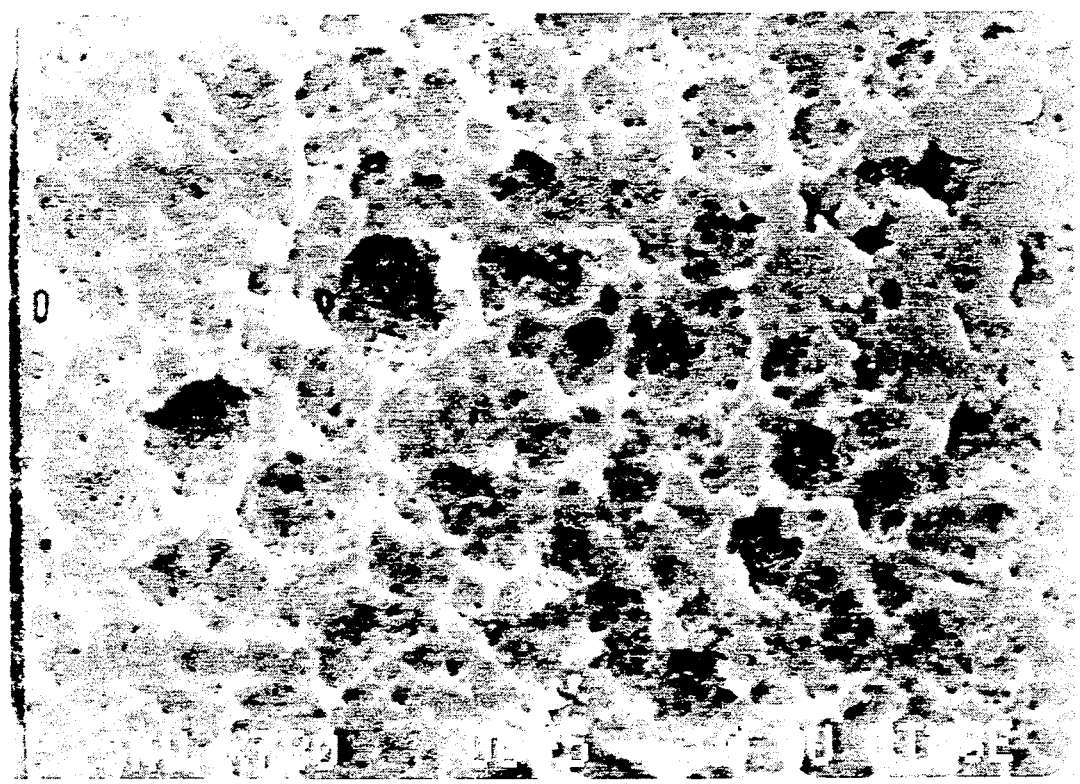
FIG. 15 shows 10% chlorpheniramine maleate, 1% proteinase K, and 90% poly(DL-lactide) 0.71 dL/g which was exposed to 0.01M Tris buffer (pH=8.0) for 24 hours.
Figure 16:
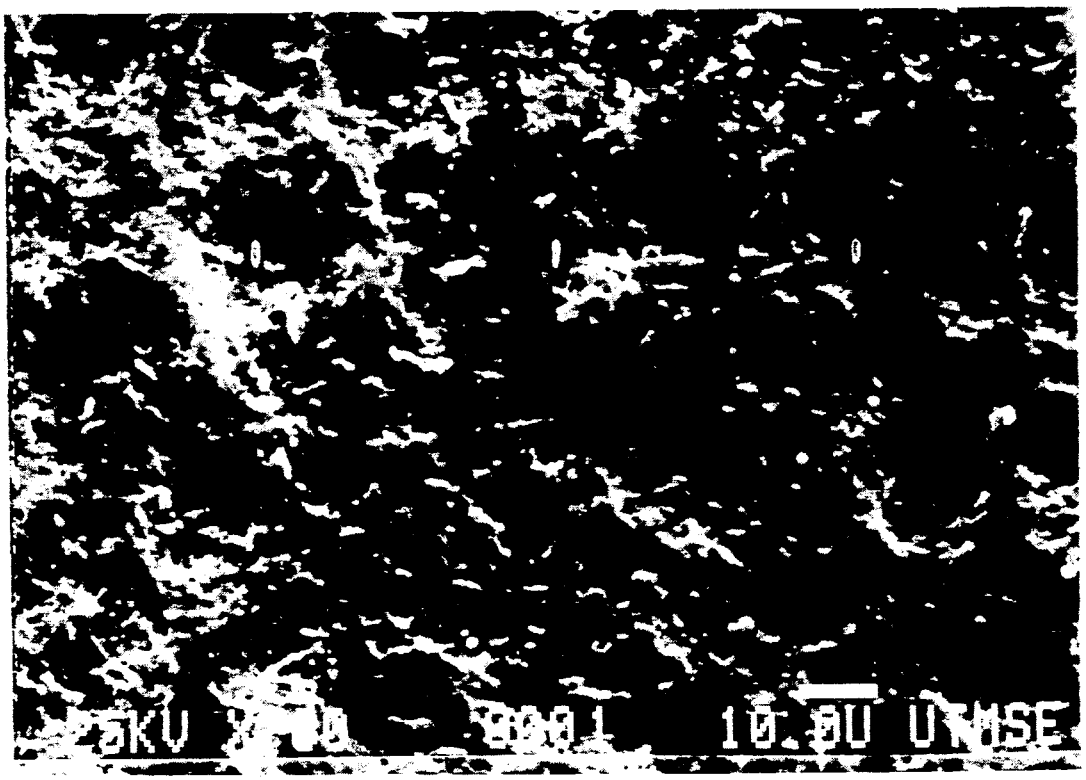
FIG. 16 shows 10% chlorpheniramine maleate, 1% proteinase K, and 90% poly(DL-lactide) 0.71 dL/g which was exposed to 0.01M Tris buffer (pH=8.0) for 24 hours—note: same slab as in FIG. 15.

The procedures as described in Examples 1 and 2 were performed but with polylactide of a lower viscosity (0.71 dL/g). FIG. 14 shows a scanning electron micrograph of the resultant slab. FIGS. 12 and 13 show a SEM of this slab after a 24 hr exposure to 0.1M Tris buffer (pH=8.0). FIGS. 15 and 16 show SEM of low viscosity poly(DL-lactide) slabs comprising 1% proteinase K after a 24 hr exposure to 0.01M Tris buffer (pH=8.0).

EXAMPLE 6

Materials and Suppliers of Materials Used to Prepare and Test Films of Poly(DL-Lactide)

Table 2 indicates the source of various reagents used in development of the present invention.

TABLE 2

| MATERIAL | SUPPLIER | DESCRIPTION OF MATERIAL |
| --- | --- | --- |
| 1. Proteinase K | Sigma Chemical Co. | Cat. #P0390-Type XI; Fungal; Lyophilized powder from Tritirachium album; Activity = 10–20 units per mg. protein (Biuret); Protein > 90%; Substantially free of DNase and RNase |
| 2. Pronase E | Sigma Chemical Co. | Cat. #P5147-type XIV; Bacterial; AN unusually non-specific protease from Streptomyces griseus; essentially starch free; contains approx. 15% calcium acetate; Activity = approx. 4 units per mg. solid |
| 3. Bromelain | Sigma Chemical Co. | Cat. #B2252-From Pineapple stem; Contains approx. 50% protein (Biuret); Activity = 2000–4000 units per gram protein; Unit definition-one unit will hydrolyze 1.0 mg of amino nitrogen from gelatin in 20 minutes at pH at 45° C. |
| 4. Chlorpheniramine Maleate | Sigma Chemical Co. | Cat. #C3025 |
| 5. Methylene Chloride | Fisher Scientific Co. | Ct. #D143-HPLC Grade; Fisher certified ACS |
| 6. Poly(DL-lactide) | Southern Research Institute | Materials tested to date have inherent viscosities of 1.23 dL/g and 0.71 dL/g (determined in chloroform) |
| 7. Trizma Base | Sigma Chemical Co. | Cat. #T1503-White crystalline powder; Mol Wt. 121.1; Primary Standard and Buffer Reagent Grade; Purity = 99.9% |

TABLE 2-continued

| MATERIAL | SUPPLIER | DESCRIPTION OF MATERIAL |
|---|---|---|
| 8. Concentrated Hydrochloric Acid | Fisher Scientific Co. | (min.) (acid-base titration) Cat. #A144-Fisher Reagent ACS |
| 9. Potassium Phosphate Dibasic | MCB Manufacturing Chemists, Inc. | Cat. #PX1570-Powder, Reagent ACS |
| 10. Potassium Phosphate Monobasic | Fisher Scientific Co. | Cat. #P285-Fisher Certified ACS |
| 11. Dipotassium Salt EDTA | Sigma Chemical Co. | Cat. #ED2P-Approx. 98% Crystalline |
| 12. L-Cysteine HCL | Sigma Chemical Co. | Cat. #C1276-Anhydrous; Crystalline |
| 13. Distilled Water-Made in the laboratory when needed | | |
| 14. Triacetin | Fluka Chemical Corp. | Cat. #90240-purum quality |
| 15. Polyvinyl-pyrrolidone K15, 30, & 90 | Fluka Chemical Corp. | Cat. #81440-purum quality |
| 16. Diethyl Phthalate | Fluka Chemical Corp. | Cat. #80080-purum quality |
| 17. Dibutyl Phthalate | Sigma Chemical Co. | Cat. #D2270 |
| 18. Dioctyl Phthalate | Fluka Chemical Corp. | Cat. #80032-purum quality |
| 19. Triethyl Citrate | Aldrich Chemical Co. | Cat. #10, 9290-99% |
| 20. Klucel LF | Hercules Inc. | Sample |

EXAMPLE 7

Suggested Method for Preparing Slabs by Compression Method

A. Micronized materials should be used.

B. Poly(DL-lactide) should be blended with therapeutic agent and enzyme for 5 minutes using the method of geometric dilution to ensure a homogeneous blend of the constituents.

C. The blended material should then be placed in a compression mold and the mold placed in a press that will allow the material to be heated prior to and during compression.

D. The press, containing the mold and material, should be heated to a temperature of 65° C.

E. The material should then be compressed at a pressure of about 10,000 lbs. for approximately 10 minutes.

F. At the end of 10 minutes, the compressed material should be cooled for 6 minutes, under compression pressure, using a combination of air and water (at room temperature) which is circulated around the compression plates.

G. At the end of the cooling cycle, the pressure is released and the plates and slab are removed from the press.

H. Note: The flexibility of the slabs produced by this method can be modified by the use of plasticizers. If plasticizers are used, they should be added during the blending stage and if solid, should be micronized as the other constituents are. The plasticizers recommended for use with the poly(DL-lactide) systems are triacetin, diethyl phthalate, triethyl citrate, and polyvinylpyrrolidone (PVP K90).

Suggested formulas for solvent casting or compression molding include:

| | |
|---|---|
| Formula #1: | Chlorpheniramine Maleate 1% w/w to 10% w/w<br>Triacetin 5% w/w to 20% w/w (recommended 10% to 15%)<br>Proteinase K 0.01% w/w to 20% w/w (recommended 2% to 5%)<br>Poly(DL-lactide) qs to 100% |
| Formula #2: | Chlorpheniramine Maleate 1% w/w to 10% w/w<br>Triethyl Citrate 5% w/w to 20% w/w (recommended 10% to 15%)<br>Proteinase K 0.01% w/w to 20% w/w (recommended 2% to 5%)<br>Poly(DL-lactide) qs to 100% |
| Formula #3: | Chlorpheniramine Maleate 1% w/w to 10% w/w<br>Diethyl Phthalate 5% w/w to 20% w/w (recommended 10% to 15%)<br>Proteinase K 0.01% w/w to 20% w/w (recommended 2% to 5%)<br>Poly(DL-lactide) qs to 100% |
| Formula #4: | Chlorpheniramine Maleate 1% w/w to 10% w/w<br>Polyvinylpyrrolidone (PVP K90) 5% w/w to 20% w/w (recommended 10% to 15%)<br>Proteinase K 0.01% w/w to 20% w/w (recommended 2% to 5%)<br>Poly(DL-lactide) qs to 100% |
| Other Enzymes: | Pronase E 0.01% w/w to 20% w/w<br>Bromelain 0.01% w/w to 20% w/w |
| Other Drugs: | Scopolamine Hydrobromide 0.01% w/w to 5% w/w |

NOTE: The formulas above can be used for slabs prepared either by the method of solvent casting or compression molding.

1. Solvent Casting Method—The therapeutic agent and plasticizer should be weighed out and dissolved in a small amount of methylene chloride. The poly(DL-lactide) should then be added to the solution and the solution brought to a final volume which will allow 5 ml. of solution to contain the required amount of each constituent. The enzyme (as a micronized powder) should then be added to this final solution (again in an amount which will allow 5 ml. of solution to contain the required amount of enzyme), stirred well, and then cast in 5 ml. quantities for each slab. The slab is allowed to dry at room temperature and then stored with desiccant.

2. Compression Molding Method—The therapeutic agent, plasticizer, and enzyme should be added to the poly(DL-lactide) by the method of geometric dilution. All materials must be micronized if solid. The mixture should then be blended for 5 minutes to ensure a homogeneous material is made for compression. The blended material is then placed in compression mold and the mold placed in press that will allow the material to be heated prior to and during compression. The compression plates, containing the mold and material, is heated to a temperature of 65° C. The material should be compressed at a pressure of 10,000 lbs. for 10 minutes. At the end of 10 minutes the compressed material is cooled for 6 minutes, under compression pressure, using a combination of air and water (at room temperature) which is circulated around the compression plates. At the end of the cooling cycle, the pressure is released and the plates and slab are removed from the press.

EXAMPLE 8

Suggested Formulas for Films Prepared with Enzyme Applied to a Slab

| Formula #1: | Bottom Layer | Chlorpheniramine Maleate 1% to 10% w/w |
| | | Triacetin 5% to 20% w/w (recommended 10% to 15%) |
| | | Poly(DL-lactide) qs to 100% w/w |
| | Top Layer | Proteinase K 0.01% to 20% w/w |
| | | Klucel LF qs to 100% w/w |
| Other Enzymes: | | Pronase E 0.01% to 20% w/w |
| | | Bromelain 0.01% to 20% w/w |
| Other Drugs: | | Scopolamine Hydrobromide 0.01% to 0.5% w/w |
| Other Plasticizers: | | Diethyl Phthalate 5% to 20% w/w (recommended 10% to 15%) |
| | | Polyvinylpyrrolidone (PVP K90) 5% to 20% w/w (recommended 10% to 15%) |

Method of Preparation

The therapeutic agent and plasticizer should be weighed out and dissolved in a small amount of methylene chloride. The poly(DL-lactide) should then be added to the solution and the solution brought to a final volume which will allow 5 ml. of solution to contain the required amount each constituent specified for the bottom layer in the formula. After mixing the solution well, 5 ml. quantities of the solution should be taken and cast to make each slab. Once cast, the methylene chloride should be allowed to evaporate and the slab to form. This will be the bottom portion of the final slab. A suspension is then made by adding the micronized enzyme to a solution of the Klucel LF in methylene chloride. The volume of methylene chloride used should be sufficient so that 2 ml. of the suspension will contain the required mounts of enzyme and Klucel LF specified in the formula for the top portion of the slab. Once made, 2 ml. of the suspension are pipetted onto the surface of the slab and spread evenly over the slab. The slab is then allowed to dry at room temperature and stored with desiccant.

EXAMPLE 9

SEM

Scanning Electron Microcopy was performed with a Joel JSM-35C scanning electron microscope (ACC Voltage=25 KV X780).

EXAMPLE 10

In Vitro Release Studies

In vitro experimental drug release studies were conducted to determine the effect of an enzyme on polymer degradation involving preparing and studying drug release from slabs which contained drug, enzyme and polymers. Prior to Applicants' laboratory studies, the effects on drug release by including any enzyme in the drug-containing polymer slab was unknown. The present study demonstrates the release-controlling potential of the inclusion of enzyme in such polymeric devices.

For example, the presence of proteinase K (enzyme) in a poly (DL-lactide) slab was found to decrease the "lag" period of drug release as well as to enhance the rate of drug release linearly with the percent of proteinase K (enzyme) included in the slab. The polymeric slabs of the present example contained proteinase K enzyme ranging from 0% to 2% by weight of the slab. Polymer degradation upon exposure to a 0.01M tris buffer, (32° C., pH 8.0) was monitored over a 180 hour test period (FIG. 17).

Materials

The polymer used in this study was poly(DL-lactide)(PLA) with inherent viscosities of 0.63, 0.71, 1.23, and 1.69 dL/g. (as determined in chloroform at a concentration of 5 mg/ml). The polymer was obtained from Southern Research Institute in Birmingham, Ala. All other materials and solvents used for film preparation and subsequent studies were purchased from various commercial sources and were used as received. These included: chlorpheniramine maleate, proteinase K, Trizma base, p-hydroxydiphenyl, rhodamine 6G dye (dye content of approximately 95%), lithium lactate (Sigma Chemical Co.); methylene chloride (HPLA grade), concentrated hydrochloric acid, calcium sulfate (8 mesh Drierite), supric sulfate, 85% phosphoric acid, sulfuric acid, sodium hydroxide, tetrahydrofuran (HPLC grade), (spectrophotometric grade, Aldrich Chemical Co.); pH 11, buffer (glycine/sodium hydroxide/sodium chloride, Fluka Chemical Corp.). All solvents and chemicals were A.C.S. reagent grade, unless otherwise indicated.

Film Preparation

Film samples containing PLA were prepared by a solvent casting method. This involved weighing a quantity of chlorpheniramine maleate (if drug was to be in the films) that was 7.5% of the total solids weight and a quantity of PLA that would bring the total solids weight to 100%. These materials were dissolved in methylene chloride (20 ml/10 g of total solids) in a tightly stoppered, pyrex bottle. Proteinase K, if added, was added at this point as a fine powder which had been produced by sieving the enzyme, as received from the manufacturer, through a #140 sieve (3 inch, U.S. Stainless Steel Standard Sieve, Thomas Scientific.). All materials were mixed well with a stirring bar which had been placed in the stoppered bottle containing the film ingredients. The resulting solution, or suspension if enzyme was present, was spread onto a piece of aluminum foil (Alufoil Products Co.) which was 0.003 inch thick. Each spread film was allowed to equilibrate at room temperature for approximately 12 hours to allow the methylene chloride present in the case mixture to evaporate. At the end of this time, each film, with its aluminum backing in place, was cut into 2 cm.×2 cm. squares for degradation studies or 4 cm.×4 cm. squares for release studies. The films, once cut, were placed in a vacuum desiccator over calcium sulfate. A vacuum of approximately 550 mm Hg was pulled on the desiccator. All films prepared in this way were used in degradation or release studies 6 to 7 days after preparation.

Results

Figure 18:
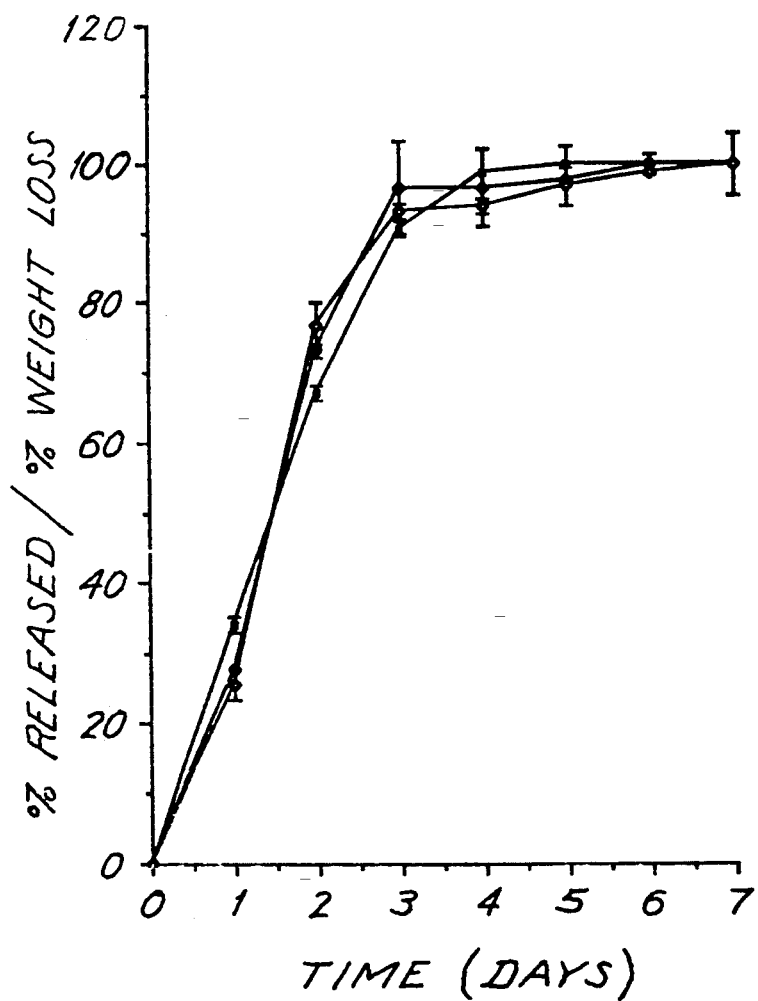
FIG. 18 shows the rate of drug release and polymeric slab weight loss in slabs containing 0.5% proteinase K enzyme over a seven day test period.

As correlated to the referenced data in FIG. 17, the presence of as little as 2% proteinase K in the polymer slab increased the rate of drug release 9-fold over non-enzyme containing slabs upon immersion in a 0.01M Tris buffer (32° C., pH 8.0) within 30 minutes. The rate of degradation of the polymeric slab was evidenced by a progressive loss in weight of the slab itself, and was correlatable to an increase in the rate of drug release observed in the test media. (FIG. 18).

Figure 19:
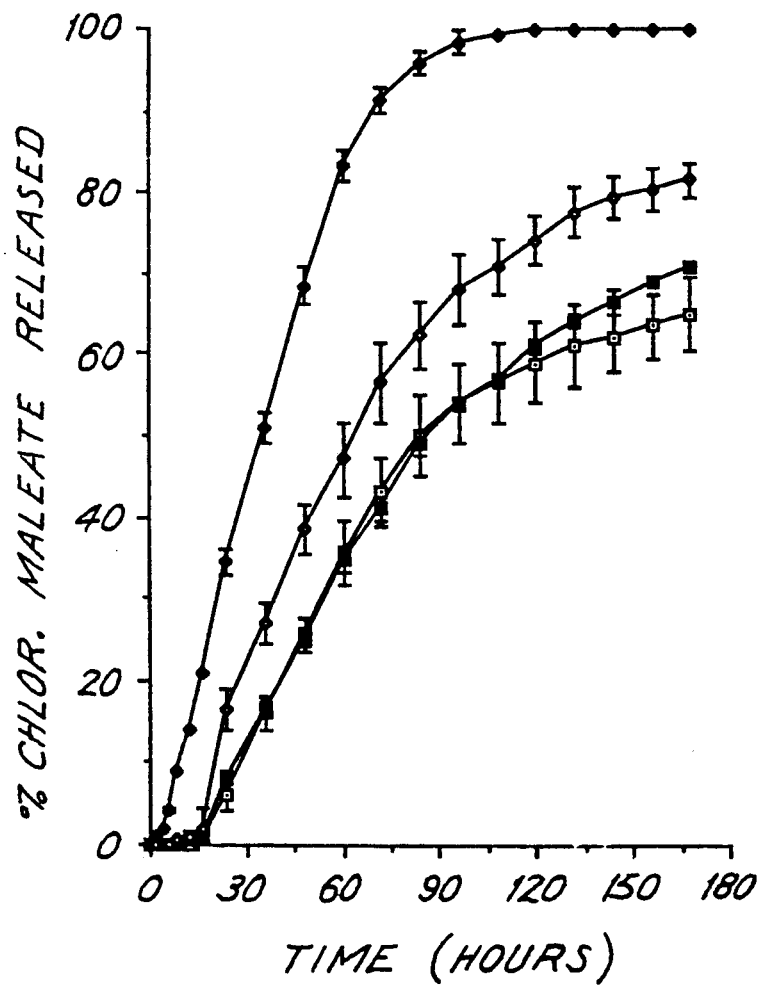
FIG. 19 shows the effect of different enzymes on drug release from a polymer slab. The enzymes compared include proteinase K, trypsin and chymotrypsin.

Data from these studies demonstrate a slower rate of polymeric breakdown in non-enzyme containing polymeric films. Additionally, comparative studies between proteinase K-containing poly (DL-lactide) slabs and chymotrypsin-, or trypsin- containing poly (DL-lactide) slabs in Example 11 demonstrated slower drug release rates from slabs with 0.5% chymotrypsin or 0.5% trypsin compared to drug release rates observed with 0.5% proteinase K-containing slabs (FIG. 19).

EXAMPLE 11

Enzyme Poly(DL-Lactide) Degradation Comparative Studies

Comparative studies between proteinase K-containing poly(DL-lactide) slabs and chymotrypsin - or trypsin - containing poly(DL-lactide) slabs were conducted. Slabs were prepared according to the methods outlined in Example 10. Slower drug release rates were demonstrated from slabs with 0.5% chymotrypsin on 5% trypsin compared to drug release rates observed with 0.5% proteinase K-containing slabs.

The data obtained from this study is presented at FIG. 19. These results suggest the enzyme proteinase K possesses the highest poly(DL-lactide) degradation, thus facilitating the greatest rate of physically-entrapped therapeutic agent therein.

Changes may be made in the elements and assemblies described herein or in the steps or the sequence of steps of the method described herein without departing from the concept and scope of the invention as defined in the following claims.

What is claimed is:

1. A pharmacologically acceptable composition of matter comprising:
   a biodegradable polymeric slab;
   a moisture activated enzyme included within the polymeric slab in a therapeutic agent releasing concentration which enzymatically degrades said slab;
   a non-polymer bound therapeutic agent incorporated into said slab,
wherein enzymatic degradation of the biodegradable polymeric slab releases the incorporated therapeutic agent at a rate which is a function of the concentration of the enzyme in the slab.

2. A pharmacologically acceptable composition of matter for the time dependent liberation of a therapeutic agent in vivo, the composition consisting essentially of:
   a biologically degradable polymeric slab;
   a non-polymer bound, homogeneously dispersed therapeutic agent physically entrapped in said polymeric slab; and
   an enzyme included at a concentration within the polymeric slab which degrades said slab in the presence of moisture to facilitate the controlled release of entrapped therapeutic agent at a rate which is a function of the concentration of the enzyme in the slab.

3. A deliver device for the transdermal administration of a therapeutic agent, said device comprising:
   a polymeric slab having a side for dermal contact;
   a non-polymer bound, homogeneously dispersed therapeutic agent physically entrapped in said polymeric slab;
   at least one moisture activated enzyme included within the slab at a concentration which provides for the controlled release of the therapeutic agent; and
   a means for holding the device in dermal contact,
wherein the therapeutic agent is released at a rate which is a function of the concentration of the enzyme within the slab.

4. The composition of claim 1 or 2 or delivery device of claim 3 wherein the polymeric slab comprises a polymer selected from the group consisting of:
   polyesters, polyamides, polypeptides, polysaccharides, cellulose, dextran, elastin, fibrin, gelatin, polyethylene, pectin, and polygalacturonic acid.

5. The composition of claim 1 or 2 or delivery device of claim 3 wherein the polymeric slab comprises a biodegradable polyester.

6. The composition of claim 1 or 2 delivery device of claim 3 wherein the polymeric slab comprises a polyester of biologically metabolizable monomeric units selected from the group consisting of lactic acid, glycolic acid, hydroxypropionic acid, and hydroxybutyric acid.

7. The composition of claim 1 or 2 or delivery device of claim 3 wherein the polymeric slab comprises a polyester of biologically metabolizable monomeric units of lactic acid or glycolic acid.

8. The composition of claim 1 or 2 or delivery device of claim 3 wherein the polymeric slab comprises a polyamide.

9. A composition of claim 1 or 2 or delivery device of claim 3 wherein the polymeric slab comprises a polypeptide.

10. The composition of claim 1 or 2 or delivery device of claim 3 wherein the enzyme hydrolyses ester bonds and comprises a hydrolase or a protease.

11. The composition of claim 1 or 2 or delivery device of claim 3 wherein the enzyme is selected from the group consisting of:
   proteinase K, bromelain, pronase E, cellulase, dextranase, elastase, plasmid, streptokinase, trypsin, chymotrypsin, papain, chymopapain, collagenase, subtilisin, ficin, carboxypeptidase A, pectinase, and pectinesterase.

12. The composition of claims 1 or 2 or delivery device of claim 3 wherein the enzyme is proteinase K, bromelain or pronase E.

13. The compositions of claim 1 or 2 or delivery device of claim 3 wherein the enzyme is proteinase K.

14. The compositions of claim 1 or 2 or delivery device of claim 3 wherein the enzyme is proteinase K at a concentration of about 0.5% by weight of the polymeric slab.

15. The device of claim 3 wherein the enzyme is dispersed on the side of the polymeric slab for contact with the dermal surface.

16. The delivery device of claim 3 wherein the means for holding the device in contact with a dermal surface is an adhesive, elastic band or bandaging tape.

17. The compositions of claim 1 or 2 or delivery device of claim 3 wherein the therapeutic agent comprises chlorpheniramine maleate.

18. A delivery device for the transdermal administration of a therapeutic agent, said device comprising:

a poly(DL-lactide) polymeric slab having a side for dermal contact;

a non-polymer bound, homogeneously dispersed therapeutic agent physically entrapped in said poly(DL-lactide) polymeric slab;

proteinase K included with the slab, which degrades the polymeric slab in the presence of moisture to release the therapeutic agent; and a means for holding the device in dermal contact selected from the group consisting of:
an adhesive;
an elastic band; and
a bandaging tape, wherein the therapeutic agent is released at a rate which is a function of the concentration of the enzyme within the slab.

* * * * *

UNITED STATES PATENT AND TRADEMARK OFFICE
CERTIFICATE OF CORRECTION

PATENT NO. : 5,227,157

DATED : July 13, 1993

INVENTORS : McGinity et al.

It is certified that error appears in the above-identified patent and that said Letters Patent is hereby corrected as shown below:

Column 20, claim 6, line 31, between the number "2" and the word "delivery," insert --or--

At claim 11, column 20, line 53, delete the term "plasmid" and substitute therefore --plasmin--.

Signed and Sealed this

Third Day of May, 1994

Attest:

Attesting Officer

BRUCE LEHMAN

Commissioner of Patents and Trademarks